US006440929B1

(12) United States Patent
Milstein et al.

(10) Patent No.: US 6,440,929 B1
(45) Date of Patent: Aug. 27, 2002

(54) PULMONARY DELIVERY OF ACTIVE AGENTS

(75) Inventors: Sam J. Milstein, Larchmont; John E. Smart, Katonah; Donald J. Sarubbi, Carmel; Monica Leipold, Thornwood, all of NY (US); Elizabeth Flanders, Ridgefield, CT (US); Doris O'Toole, Carmel, NY (US); Andrea Leone-Bay, Ridgefield, CT (US); David Gschneidner, Stamford, CT (US)

(73) Assignee: Emisphere Technologies, Inc., Tarrytown, NY (US)

( * ) Notice: Subject to any disclaimer, the term of this patent is extended or adjusted under 35 U.S.C. 154(b) by 0 days.

(21) Appl. No.: 09/744,777

(22) PCT Filed: Jul. 27, 1999

(86) PCT No.: PCT/US99/16957

§ 371 (c)(1), (2), (4) Date: Apr. 26, 2001

(87) PCT Pub. No.: WO00/06184

PCT Pub. Date: Feb. 10, 2000

Related U.S. Application Data

(60) Provisional application No. 60/104,466, filed on Oct. 16, 1998, and provisional application No. 60/094,267, filed on Jul. 27, 1998.

(51) Int. Cl.[7] ...................... A61K 38/00; A61K 31/725; A61K 31/195

(52) U.S. Cl. ................................ 514/2; 514/3; 514/11; 514/12; 514/21; 514/56; 514/563

(58) Field of Search ........................... 514/2, 3, 11, 12, 514/21, 56, 563

(56) References Cited

U.S. PATENT DOCUMENTS

| | | | |
|---|---|---|---|
| 4,147,767 A | 4/1979 | Yapel | 424/22 |
| 4,238,506 A | 12/1980 | Stach et al. | 424/319 |
| 4,757,066 A | 7/1988 | Shiokari et al. | 514/210 |

(List continued on next page.)

FOREIGN PATENT DOCUMENTS

| | | |
|---|---|---|
| EP | 0036145 | 9/1981 |
| EP | 226223 | 6/1987 |
| EP | 0517211 | 9/1992 |
| EP | 576941 | 6/1993 |
| ES | 369853 | 7/1969 |
| GB | 2095994 | 10/1982 |
| JP | 2239980 | 9/1990 |
| WO | 0006184 | 2/2000 |
| WO | 0006534 | 2/2000 |
| WO | 0007979 | 5/2000 |
| WO | 0048589 | 8/2000 |
| WO | 0059863 | 10/2000 |

OTHER PUBLICATIONS

Picciola G.: "Sintesi Di Acidi Chiazolinioici E Benzossazinonici E Studio Delle Loro Proprieta Antiniammatorie" IT, Societa Chimica Italiana Pavia vol. 31, No. 9 pp. 655–664 and English Translation (no date available).

Chem Abs 73548–12–6 (Apr. 1991).

Chem Abs 70204–54–5 (Apr. 1991).

Chem Abs 184360–83–342 (1975) Solubility and disassociation constants of some alicyclic acids.

Chemical Abstract, vol. 99(23) Abst. No. 191473h (1983).

Johansen, Marianne, et al. "The Kinetics of decompn. Of various N–Mannich bases of salicylamide" Int. J. Pharm. (1980), 7(2): 119–27 (1980).

Riveria, Theresa M. et al. "Oral Delivery of Heparin in Combination with sodium N–[8–2–hydroxybenzoyl)amino] caprylate: Pharmacological Considerations" Pharmaceutical Research vol. 14(12) 1830–1834 (1997).

Andrea Leone–Bay"4–(4–Salicyloylaminophenyl)butyric Acid as a Novel Oral Delivery Agent for Recombinant Human Growth Hormone" Medi 006, Presented at the American Chemical Society, Mar. 24–28, (1997) New Orleans, LA.

Leone–Bay, A. et al. "The evolution of an oral heparin dosing solution" Drugs of the Future vol. 22(8) 885–891 (1997).

Brayden, D. et al. "Heparin Absorption across the intestin: Effects of sodium N–[8–2hydorxybenzoyl)Amino] Caprylate in rat in situ intestinal instillations ind in Caco–2 monolayers" Pharmaceutical Research vol. 14(12) 1772–1779 (1997).

Leone–Bay, A. "Acylated non–alpha–amino acids as novle agents for the oral delivery of heparin sodium, USP" Journal of Controlled Release 50: 41–49 (1998).

Leone–Bay, A. "4–[4–[(2–Hydroxybenzoyl)amino]phenyl] butyric acid as a novel oral delivery agent for recombinant human growth hormone"; Journal of Medicinal Chemistry vol. 39, 2571–2578 (1996).

Leone–Bay, A. "N–Acylated alpha–amino acids as novel oral delivery agents for proteins"; Journal of Medicinal Chemistry vol. 38, 4263–4269 (1995).

Leone–Bay, A. "N–Acylated alpha–amino acids as novel oral delivery agents for proteins"; Journal of Medicinal Chemistry vol. 38, 4257–4262 (1995).

Ho Koc–Kan; et al. "A Practical Synthesis of ω–aminoalkanoic acid derivatives form Cycloalkanones" Synthetic Communication, vol. 26, No. 14: 2641–2649 (1996).

Gurrieri and Siracusa: "Thermal Condensation of Some alpha–aminoacids with Phatalic Acid" Thermochimica Acta, 7 (1973) 231–239.

Amino Yusuke et al. Chem Pharm Bull 36 pp. 4426–4434 (1988).

Brown, G. and Foubister, A.J. Receptor Binding Sites of Hypoglycemic Sulfonylureas and Related[(Acylamino)alkyl []benzoic Acids JmedChem 27, 79–81(1984).

*Primary Examiner*—Raymond Henley, III
(74) *Attorney, Agent, or Firm*—Darby & Darby

(57) ABSTRACT

The present invention relates to pulmonary delivery of active agents. Acylated or sufonated amino acids are used as carriers to facilitate pulmonary delivery of active agents to a target.

17 Claims, 9 Drawing Sheets

U.S. PATENT DOCUMENTS

| | | | | |
|---|---|---|---|---|
| 4,873,087 | A | 10/1989 | Morishita et al. | 424/433 |
| 4,895,725 | A | 1/1990 | Kantor et al. | 424/455 |
| 4,925,673 | A | 5/1990 | Steiner | 424/491 |
| 4,976,968 | A | 12/1990 | Steiner | 424/491 |
| 4,983,402 | A | 1/1991 | Steiner | 424/491 |
| 5,066,487 | A | 11/1991 | Morelle et al. | 424/68 |
| 5,352,461 | A | 10/1994 | Feldstein et al. | 424/493 |
| 5,401,516 | A | 3/1995 | Milstein et al. | 424/491 |
| 5,443,841 | A | 8/1995 | Milstein et al. | 424/451 |
| 5,447,728 | A | 9/1995 | Milstein et al. | 424/490 |
| 5,451,410 | A | 9/1995 | Milstein et al. | 424/490 |
| 5,455,335 | A | 10/1995 | Kahane et al. | 536/5 |
| 5,540,939 | A | 7/1996 | Milstein et al. | 424/491 |
| 5,541,155 | A | 7/1996 | Leone-Bay et al. | 514/2 |
| 5,578,323 | A | 11/1996 | Milstein et al. | 424/499 |
| 5,601,846 | A | 2/1997 | Milstein et al. | 424/499 |
| 5,629,020 | A | 5/1997 | Leone-Bay et al. | 424/489 |
| 5,643,957 | A | 7/1997 | Leone-Bay et al. | 514/563 |
| 5,650,386 | A | 7/1997 | Leone-Bay et al. | 514/2 |
| 5,667,806 | A | 9/1997 | Kantor et al. | 424/484 |
| 5,693,338 | A | 12/1997 | Milstein et al. | 424/451 |
| 5,705,529 | A | 1/1998 | Matyus et al. | 514/541 |
| 5,709,861 | A | 1/1998 | Santiago et al. | 424/184 |
| 5,714,167 | A | 2/1998 | Milstein et al. | 424/490 |
| 5,750,147 | A | 5/1998 | Kantor et al. | 424/491 |
| 5,766,633 | A | 6/1998 | Milstein et al. | 424/489 |
| 5,773,647 | A | 6/1998 | Leone-Bay et al. | 562/444 |
| RE35,862 | E | 7/1998 | Steiner et al. | 424/455 |
| 5,776,888 | A | 7/1998 | Leone-Bay et al. | 514/2 |
| 5,792,451 | A | 8/1998 | Sarubbi et al. | 424/85.4 |
| 5,804,688 | A | 9/1998 | Leone-Bay et al. | 562/444 |
| 5,811,127 | A | 9/1998 | Milstein et al. | 424/490 |
| 5,820,881 | A | 10/1998 | Milstein et al. | 424/489 |
| 5,824,345 | A | 10/1998 | Milstein et al. | 424/489 |
| 5,840,340 | A | 11/1998 | Milstein et al. | 424/499 |
| 5,863,944 | A | 1/1999 | Leone-Bay et al. | 514/559 |
| 5,866,536 | A | 2/1999 | Leone-Bay et al. | 514/2 |
| 5,876,710 | A | 3/1999 | Leone-Bay et al. | 424/85.1 |
| 5,879,681 | A | 3/1999 | Leone-Bay et al. | 424/85.1 |
| 5,935,601 | A | 8/1999 | Leone-Bay et al. | 424/489 |
| 5,939,381 | A | 8/1999 | Leone-Bay et al. | 514/2 |
| 5,955,503 | A | 9/1999 | Leone-Bay et al. | 514/563 |
| 5,958,457 | A | 9/1999 | Santiago et al. | 424/490 |
| 5,962,710 | A | 10/1999 | Gschneidner et al. | 554/112 |
| 5,965,121 | A | 10/1999 | Leone-Bay et al. | 424/85.2 |
| 5,972,387 | A | 10/1999 | Milstein et al. | 424/491 |
| 5,976,569 | A | 11/1999 | Milstein et al. | 424/451 |
| 5,989,539 | A | 11/1999 | Leone-Bay et al. | 424/85.2 |
| 5,990,166 | A | 11/1999 | Leone-Bay et al. | 514/563 |
| 6,001,347 | A | 12/1999 | Leone-Bay et al. | 424/85.1 |
| 6,051,258 | A | 4/2000 | Kantor | 424/491 |
| 6,051,561 | A | 4/2000 | Leone-Bay et al. | 514/56 |
| 6,060,513 | A | 5/2000 | Leone-Bay et al. | 514/559 |
| 6,071,510 | A | 6/2000 | Leone-Bay et al. | 424/85.2 |
| 6,071,538 | A | 6/2000 | Milstein et al. | 424/464 |
| 6,084,112 | A | 7/2000 | Ho et al. | 554/114 |
| 6,090,958 | A | 7/2000 | Milstein et al. | 554/112 |
| 6,099,856 | A | 8/2000 | Milstein et al. | 424/450 |
| 6,100,285 | A | 8/2000 | Kantor | 514/400 |
| 6,100,298 | A | 8/2000 | Leone-Bay et al. | 514/563 |
| 6,180,140 | B1 | 1/2001 | Leone-Bay et al. | 424/489 |
| 6,221,367 | B1 | 4/2001 | Milstein et al. | 424/400 |

PULMONARY DELIVERY OF ACTIVE AGENTS

This application is a national phase application under 35 U.S.C. §371 of PCT Application No. PCT/US99/16957, filed Jul. 27, 1999 and published as International Publication No. WO 00/06184, which claims the benefit of U.S. Provisional Application No. 60/094,267, filed Jul. 27, 1998, and U.S. Provisional Application No. 60/104,466, filed Oct. 16, 1998.

FIELD OF THE INVENTION

The present invention relates to pulmonary delivery of active agents. Acylated or sulfonated amino acids are used as carriers to facilitate pulmonary delivery of active agents to a target.

BACKGROUND OF THE INVENTION

Conventional means for delivering active agents are often severely limited by biological, chemical, and physical barriers. Typically, these barriers are imposed by the environment through which delivery occurs, the environment of the target for delivery, or the target itself. Biologically or chemically active agents are particularly vulnerable to such barriers.

For example, in the delivery to animals of biologically active or chemically active pharmacological and therapeutic agents, barriers are imposed by the body. Examples of physical barriers are the skin and various organ membranes that must be traversed before reaching a target. Chemical barriers include, but are not limited to, pH variations, lipid bi-layers, and degrading enzymes.

Pulmonary delivery to the circulatory system for many biologically active agents could be the route of choice for administration to animals because delivery to the blood is much more rapid than with other routes of delivery. In addition, delivery to the lung itself may be desired, e.g., for treatment of ailments of the pulmonary system. However, pulmonary delivery may not be practical because of physical barriers such as lipid bi-layers, and membranes that are relatively impermeable to certain biologically active agents, but which must be traversed before an agent can reach the circulatory system. In other cases, pulmonary delivery may be achieved, but not efficiently enough for practical purposes.

There is presently a need for simple, inexpensive pulmonary delivery systems which are easily prepared and which can deliver a broad range of active agents in an efficient manner.

0.05 mg/kg (0.13 U/kg) (♦) and combined with Carrier B 16 mg/kg (■). Bars represent ±SD n=3.

Figure 4:
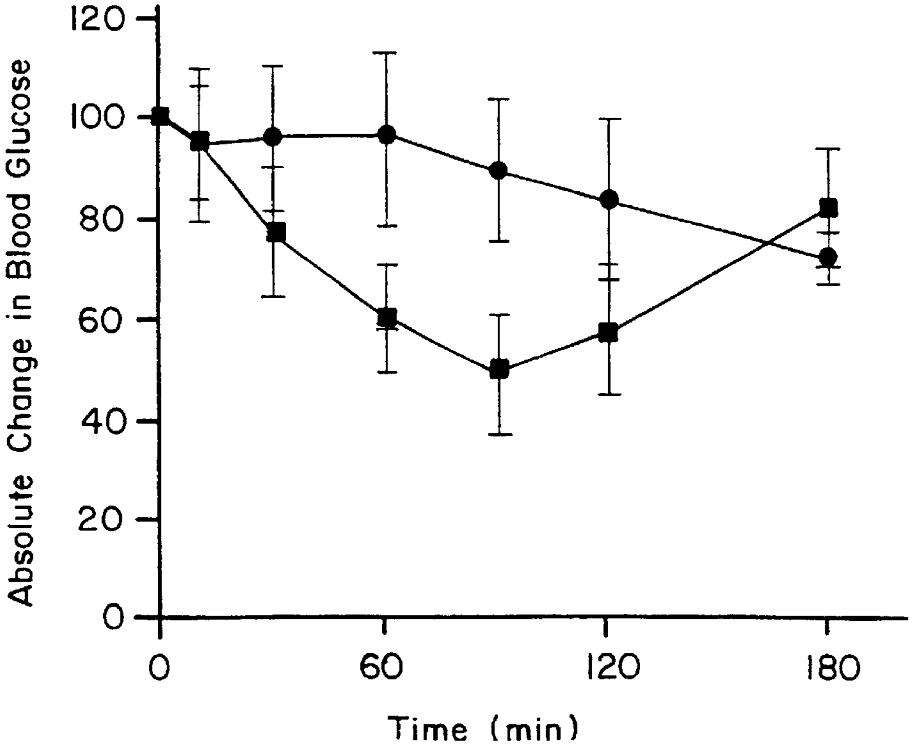

FIG. 4 is a graphical illustration of plasma glucose-time profiles following lung spray-IT instillation of insulin alone 0.01 mg/kg (0.026 U/kg) (♦) and combined with Carrier B 16 mg/kg, (■). Bars represent ±SD n=4.

Figure 5:
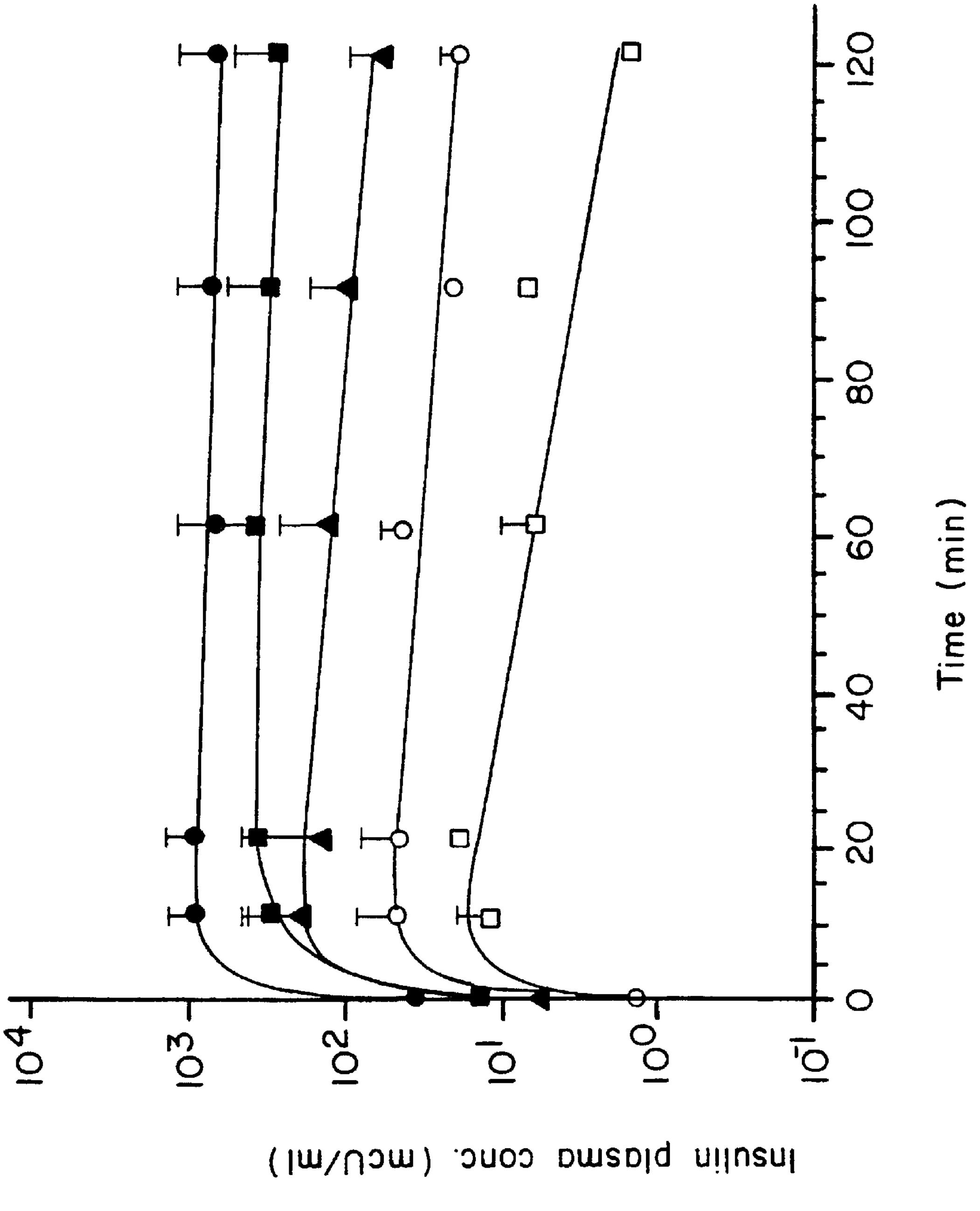

FIG. 5 is a graphical illustration of insulin average plasma concentration over time following lung spray-IT instillation of 0.005 mg/kg (0.013 U/kg) (*), 0.05 mg/kg (0.13 U/kg) (♦), 0.1 mg/kg (0.26 U/kg) (▲), 0.5 mg/kg (1.3 U/kg) (■), and 1 mg/kg (2.6 U/kg) (●) porcine insulin to rats. Bars represent ±SD.

Figure 6:
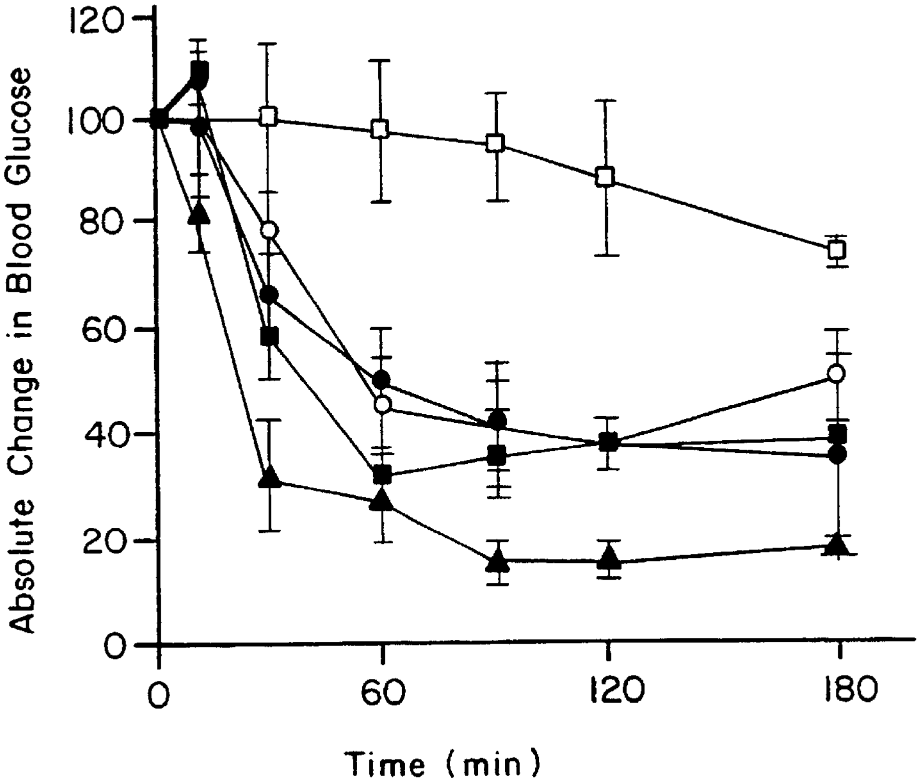

FIG. 6 is a graphical illustration of plasma glucose-time profiles following spray-IT instillation of 0.01 mg/kg (0.026 U/kg) (*), 0.05 mg/kg (0.13 U/kg) (x), 0.1 mg/kg (0.26 U/kg) (♦), 0.5 mg/kg (1.3 U/kg) (■), and 1 mg/kg (2.6 U/kg) (▲) porcine insulin to rats. Bars represent ±SD.

Figure 7:
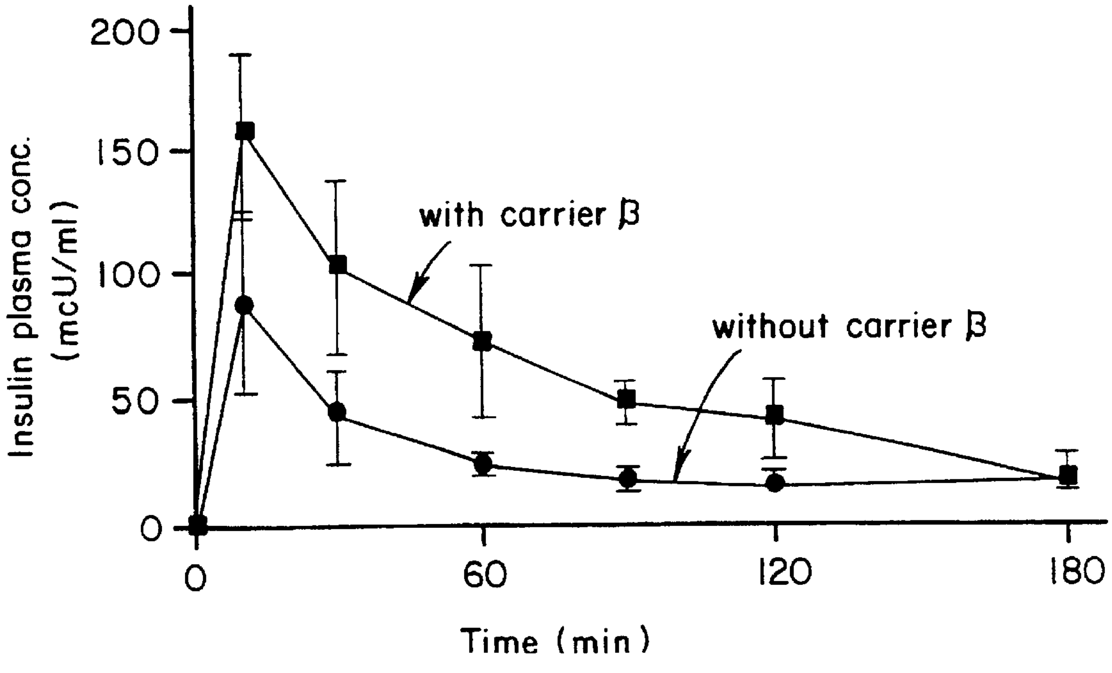

FIG. 7 is a graphical illustration of insulin plasma concentration over time of 0.05 mg/kg insulin with and without Carrier B 16 mg/kg.

Figure 8:
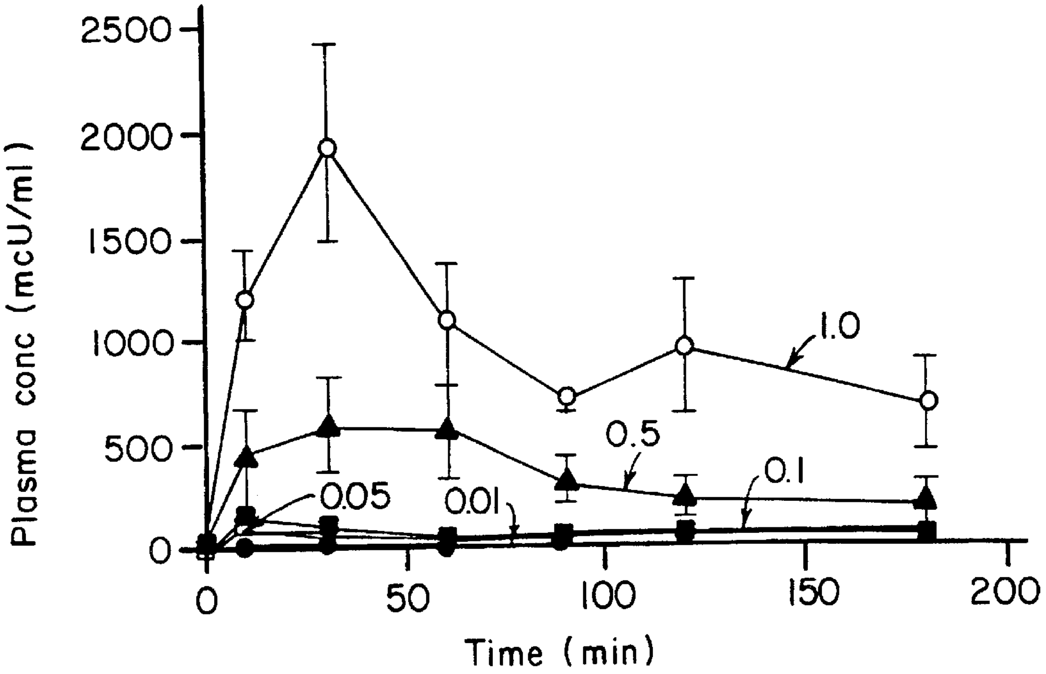

FIG. 8 is a graphical illustration of insulin plasma concentration over time with varying dose of insulin.

Figure 9:
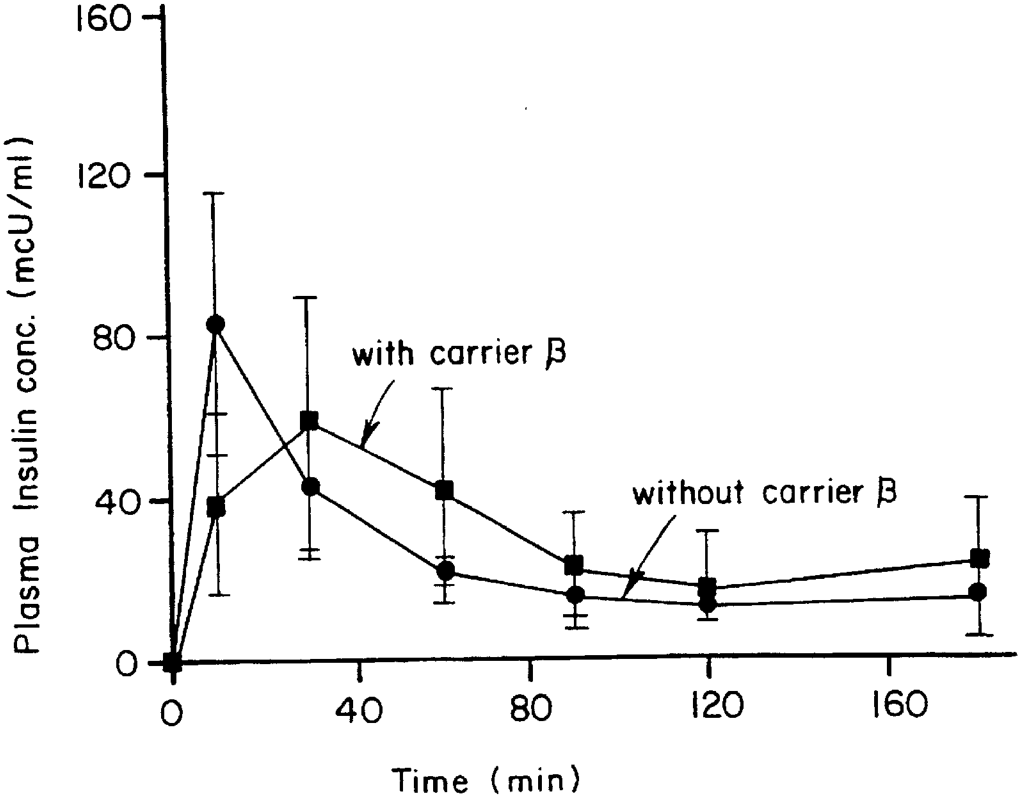

FIG. 9 is a graphical illustration of insulin plasma concentration over time of 0.05 mg/kg insulin with and without Carrier B 5 mg/kg.

Figure 10:
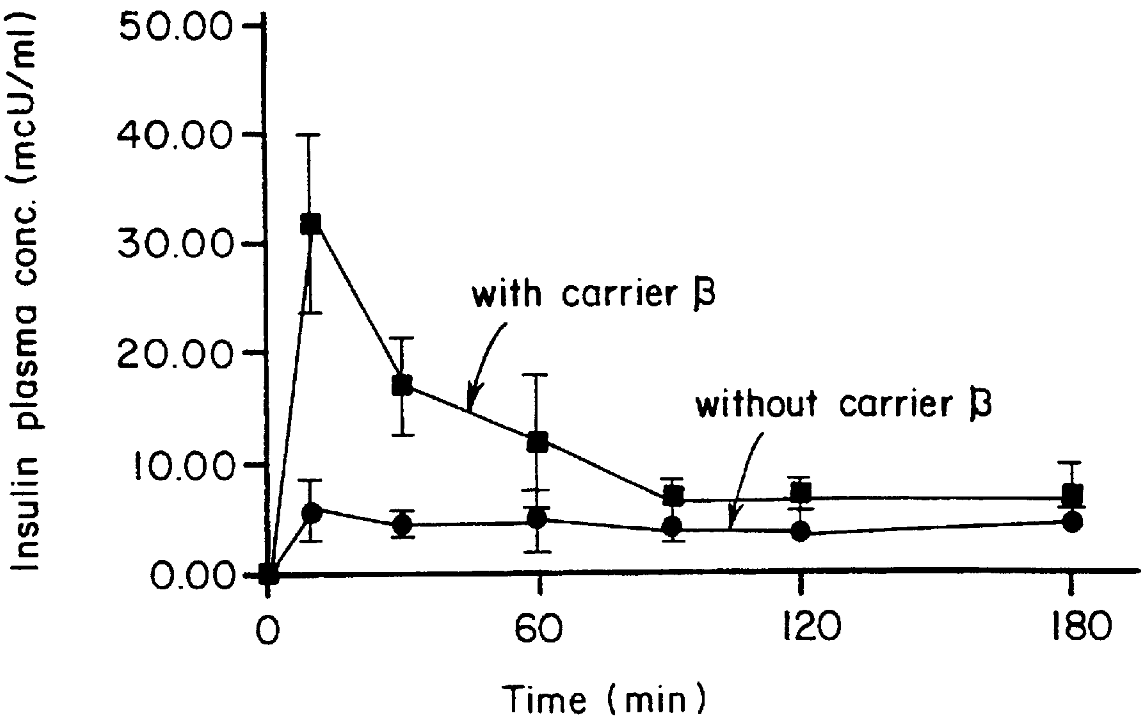

FIG. 10 is a graphical illustration of insulin plasma concentration over time of 0.01 mg/kg insulin with and without Carrier B 16 mg/kg.

Figure 11:
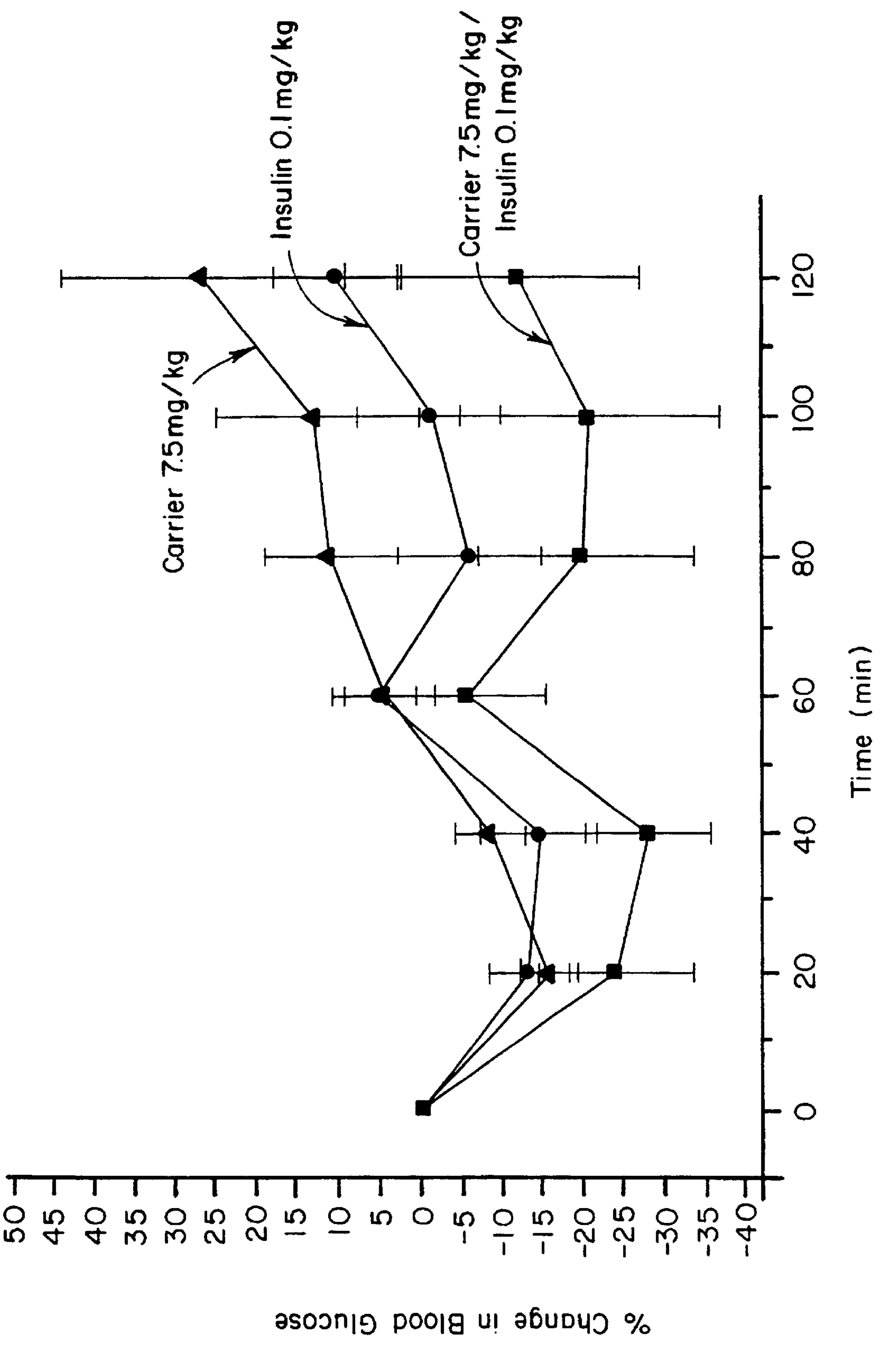

FIG. 11 is a graphical illustration of percent change in blood glucose following pulmonary delivery of 0.1 mg insulin with 7.5 mg/kg Carrier B sodium salt (■), 0.1 mg/kg insulin alone (●), and 7.5 mg/kg Carrier B sodium salt alone (▲).

Figure 12:
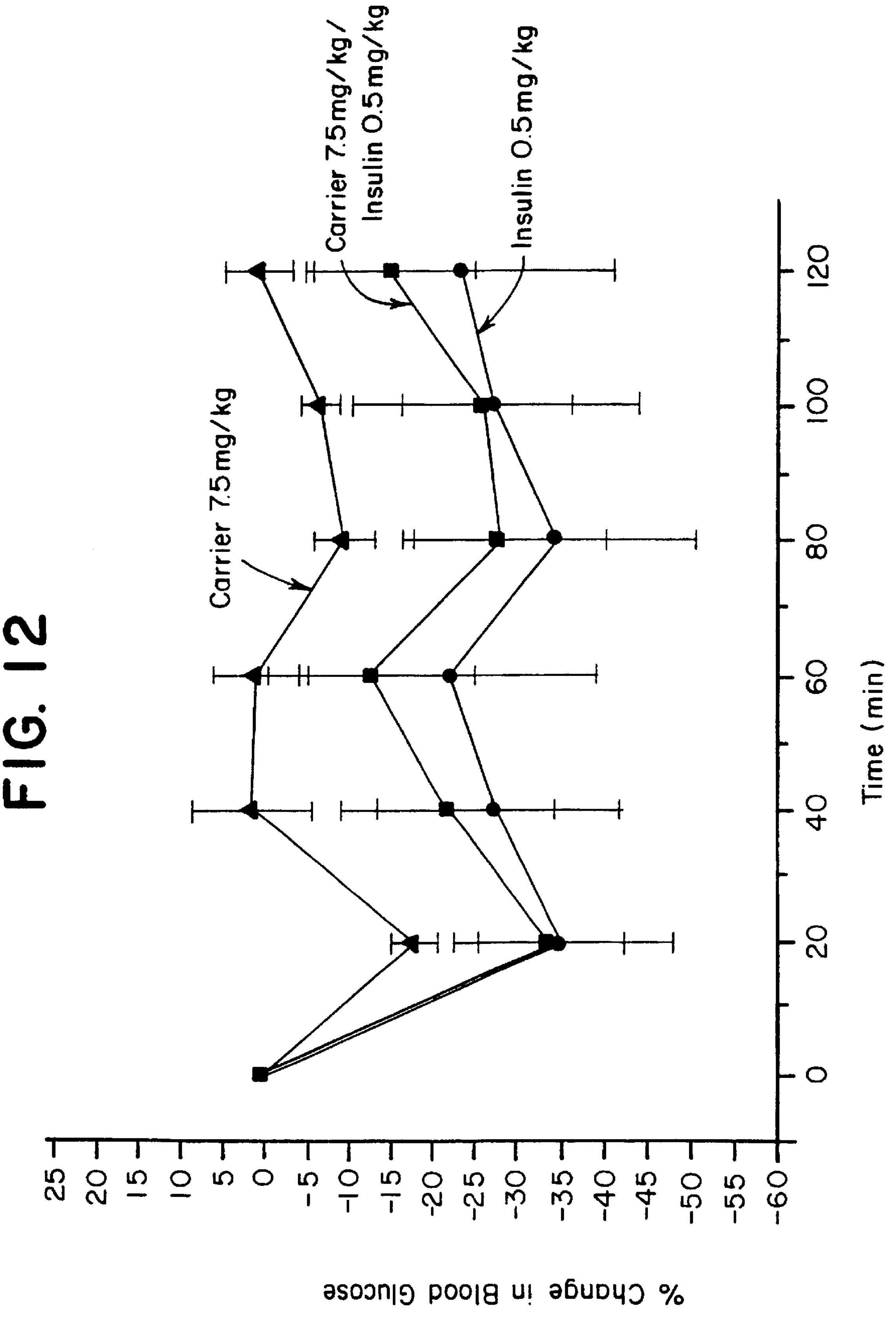

FIG. 12 is a graphical illustration of percent change in blood glucose following pulmonary delivery of 0.5 mg insulin with 7.5 mg/kg Carrier B sodium salt (■), 0.5 mg/kg insulin alone (●), and 7.5 mg/kg Carrier B sodium salt alone (▲).

Figure 13:
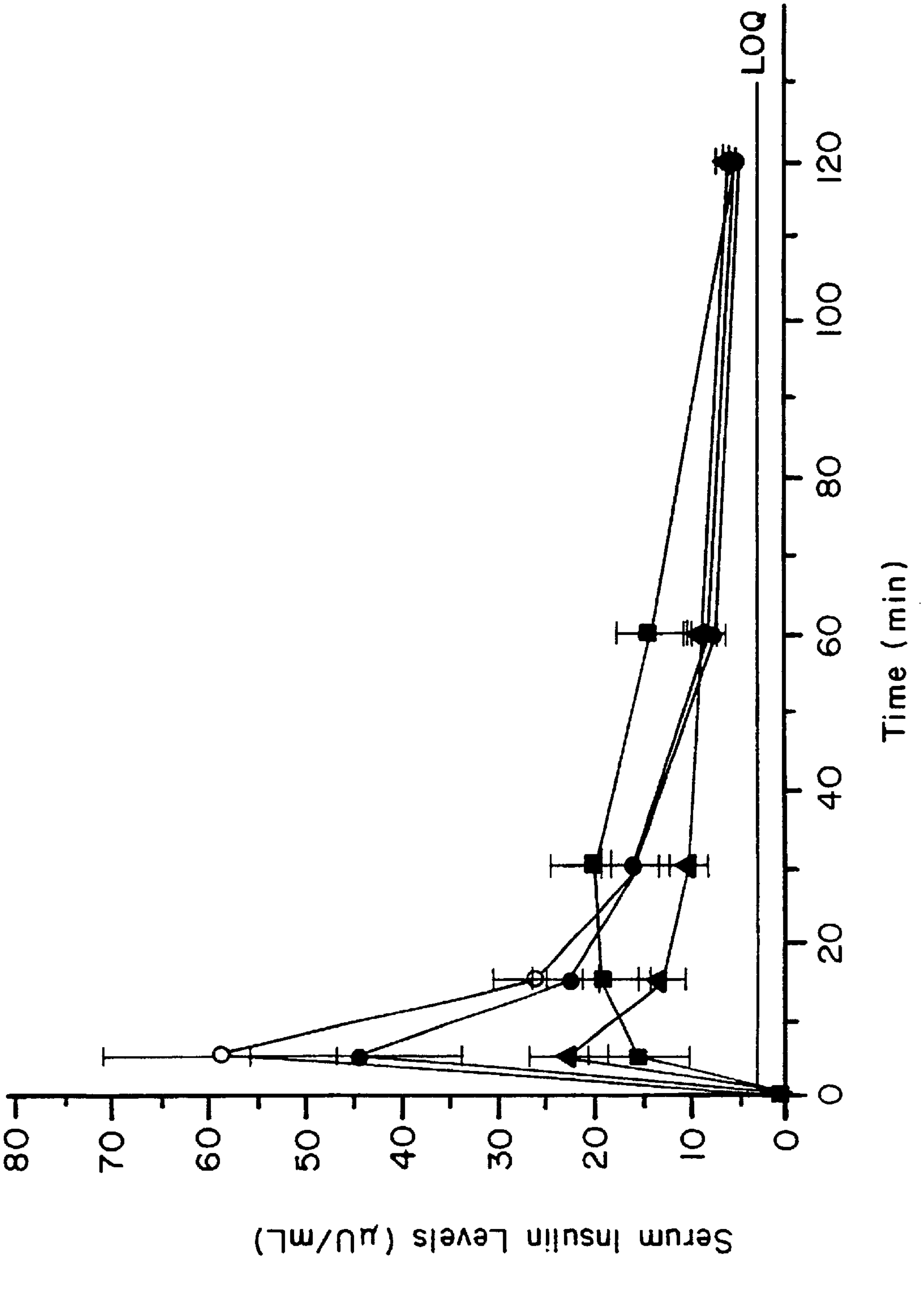

FIG. 13 is a graphical illustration of serum insulin levels over time of 0.03 mg/kg insulin with 16 mg/kg Carrier B (●), Carrier C (▲), and Carrier D (▼), and insulin alone (■). Bars represent ±SD.

SUMMARY OF THE INVENTION

The present invention provides methods for administering an active agent to an animal in need of the agent by the pulmonary route. This method comprises administering via the pulmonary route, a composition comprising (a) an active agent and (b)(i) an acylated amino acid, (ii) a sulfonated amino acid, or (iii) a combination of (i) and (ii). Administration of the compositions of the present invention provide improved pulmonary delivery and greater bioavailability of the active agent than administration of the active agent alone. As a result, lesser amounts of the active agent may be administered to obtain a desired result when contained in the composition of the present invention than when administered alone.

DETAILED DESCRIPTION OF THE INVENTION

Compositions useful in the present invention include an active agent and a carrier. These compositions may be used to deliver various active agents through various biological, chemical, and physical barriers and are particularly suited for delivering active agents which are subject to environmental degradation. The methods of the subject invention are particularly useful for delivering or administering biologically, pharmacologically, or chemically active agents to any animal, including, but not limited to, birds, such as chickens, and mammals, such as cows, pigs, dogs, cats, primates, and particularly humans.

Pulmonary coadministration of a carrier with an active agent, such as, for example insulin as described herein results in an increased bioavailability of the active agent compared to administration of the active agent alone.

Active Agents

Active agents suitable for use in the present invention include biologically or chemically active agents.

Biologically or chemically active agents include, but are not limited to, pesticides, pharmacological agents and therapeutic agents. For example, biologically or chemically active agents suitable for use in the present invention include, but are not limited to, proteins; polypeptides; peptides; hormones, and particularly hormones which by themselves do not or only a fraction of the administered dose passes through the alveoli of the lung and/or are susceptible to chemical cleavage by acids and enzymes in the lung; polysaccharides, and particularly mixtures of mucopolysaccharides; carbohydrates; lipids; other organic compounds; or any combination thereof.

Further examples include, but are not limited to, the following, including synthetic, natural or recombinant sources thereof; growth hormones, including human growth hormones (hGH), recombinant human growth hormones (rhGH), bovine growth hormones, and porcine growth hormones; growth hormone-releasing hormones; interferons, including α, β and γ; interleukin-1; interleukin II; insulin, including porcine, bovine, human and human recombinant, optionally having counter ions including sodium, zinc, calcium, and ammonium; insulin-like growth factor (IGF), including IGF-1; heparin, including unfractionated heparin, heparinoids, dermatans, chondroitins, low molecular weight heparin, very low molecular weight heparin and ultra low molecular weight heparin; calcitonin, including salmon, eel and human; erythropoietin; atrial natureic factor; antigens; monoclonal antibodies; somatostatin; protease inhibitors; adrenocorticotropin, gonadotropin releasing hormone; oxytocin; leutinizing-hormone-releasing-hormone; follicle stimulating hormone; glucocerebrosidase; thrombopoietin; filgrastim; prostaglandins; cyclosporin; vasopressin; cromolyn sodium (sodium or disodium chromoglycate); vancomycin; desferrioxamine (DFO); parathyroid hormone (PTH), including its fragments; antimicrobials, including anti-fungal agents; analogs, fragments, mimetics or polyethylene glycol (PEG)-modified derivatives of these compounds; or any combination thereof.

Carriers

Acylated and sulfonated amino acids have been found to act as carriers for pulmonary delivery of biologically or chemically active agents. These carrier compounds or poly amino acids and peptides, may be used to deliver active agents including, but not limited to, biologically or chemically active agents, such as for example, pharmacological and therapeutic agents.

An amino acid is any carboxylic acid having at least one free amine group and includes naturally occurring and synthetic amino acids. Poly amino acids are either peptides or two or more amino acids linked by a bond formed by other groups which can be linked, e.g. an ester, anhydride, or an anhydride linkage. Peptides are two or more amino acids joined by a peptide bond. Peptides can vary in length from dipeptides with two amino acids to polypeptides with several hundred amino acids. See *Chambers Biological Dictionary,* editor Peter M. B. Walker, Cambridge, England: Chambers Cambridge, 1989, page 215. Special mention is made of di-peptides, tri-peptides, tetra-peptides, and penta-peptides.

Amino acids may be used to prepare the carriers useful in the present invention. An amino acid is any carboxylic acid having at least one free amine group and includes naturally occurring and synthetic amino acids. Many amino acids and amino acid esters are readily available from a number of commercial sources such as Aldrich Chemical Co. (Milwaukee, Wis, USA); Sigma Chemical Co. (St. Louis. Mo., USA); and Fluka Chemical Corp. (Ronkonkoma, N.Y., USA). Peptides can be homo- or hetero-peptides and can include natural amino acids, synthetic amino acids, or any combination thereof.

Modified amino acids, poly amino acids, or peptides are either acylated or sulfonated and include amino acid amides and sulfonamides.

Special mention is made of acylated or sulfonated amino acids having the formula Carrier A

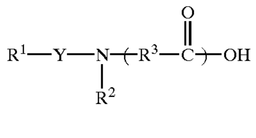

wherein $R^1$ is $C_1$–$C_7$ alkyl, $C_3$–$C_{10}$ cycloalkyl, cycloalkenyl, aryl, thienyl, phenyl, naphthyl, pyrrolo, or pyridyl;

$R^1$ is optionally substituted with one or more $C_1$–$C_7$ alkyl, $C_2$–$C_7$ alkenyl, $C_2$–$C_7$ alkynl, $C_6$–$C_{10}$ cycloalkyl, phenyl, phenoxy, F, Cl, Br, —OH, —$SO_2$, —$SO_3H$, —$NO_2$, —SH, —$PO_3H$, oxazolo, isoxazolo, alkoxy having the formula —$OR^6$, —$COOR^7$, —$N(R^5)_2$, —$N^+(R^5)_3X$, or any combination thereof;

Y is

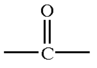

or —$SO_2$—;

X is halogen, hydroxide, sulfate, tetrafluoroborate, or phosphate;

$R^2$ is hydrogen, $C_1$–$C_4$ alkyl, $C_2$–$C_4$ alkenyl, or —$(CH_2)_n$—COOH, where n is 1 to 10;

$R^3$ is $C_1$–$C_{24}$ alkyl, $C_2$–$C_{24}$ alkenyl, $C_2$–$C_{24}$ alkyne, $C_3$–$C_{10}$ cycloalkyl, $C_3$–$C_{10}$ cycloalkenyl, phenyl, naphthyl, ($C_1$–$C_{10}$ alkyl) phenyl, ($C_2$–$C_{10}$ alkenyl) phenyl, ($C_1$–$C_{10}$ alkyl) naphthyl, ($C_2$–$C_{10}$ alkenyl) naphthyl, phenyl ($C_1$–$C_{10}$ alkyl), phenyl ($C_2$–$C_{10}$ alkenyl), naphthyl ($C_1$–$C_{10}$ alkyl) or naphthyl ($C_2$–$C_{10}$ alkenyl);

$R^3$ being optionally substituted with $C_1$–$C_4$ alkyl, $C_2$–$C_4$ alkenyl, $C_1$–$C_4$ alkoxy, —OH, —SH, halogen, —$NH_2$, —$CO_2R^4$, $C_3$–$C_{10}$ cycloalkyl, $C_3$–$C_{10}$ cycloalkenyl, heterocyclic having 3–10 ring atoms wherein the hetero atom is one or more of N, O, S or any combination thereof, aryl, ($C_1$–$C_{10}$ alk)aryl, ar($C_1$–$C_{10}$ alkyl), or any combination thereof;

$R^4$ is hydrogen, $C_1$–$C_4$ alkyl, or $C_2$–$C_4$ alkenyl;

$R^5$ is hydrogen or $C_1$–$C_{10}$ alkyl;

$R^6$ is $C_1$–$C_{10}$ alkyl, alkenyl, alkynyl, aryl or cycloalkyl; and $R^7$ is hydrogen, $C_1$–$C_{10}$ alkyl, alkenyl, alkynl, aryl or cycloalkyl.

Special mention is also made of acylated or sulfonated amino acids having the formula $Ar—Y—(R^8)_n—OH$ Carrier A' wherein

Ar is a substituted or unsubstituted phenyl or naphthyl, preferably Ar is substituted or unsubstituted 2-OH-phenyl;

Y is

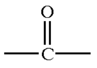

or —$SO_2$—;

$R^8$ has the formula

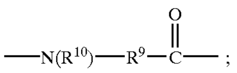

$R^9$ is $C_1$ to $C_{24}$ alkyl, $C_1$ to $C_{24}$ alkenyl, phenyl, naphthyl, ($C_1$ to $C_{10}$ alkyl) phenyl, ($C_1$–$C_{10}$ alkenyl) phenyl, ($C_1$ to $C_{10}$ alkyl) naphthyl, ($C_1$ to $C_{10}$ alkenyl) naphthyl, phenyl ($C_1$ to $C_{10}$ alkyl), phenyl ($C_1$ to $C_{10}$ alkenyl), naphthyl ($C_1$ to $C_{10}$ alkyl) and naphthyl ($C_1$ to $C_{10}$ alkenyl);

$R^9$ is optionally substituted with $C_1$ to $C_4$, alkyl, $C_1$ to $C_4$ alkenyl, $C_1$ to $C_4$ alkoxy, —OH, —SH, —$CO_2R^{11}$, cycloalkyl, cycloalkenyl, heterocyclic alkyl, alkaryl, heteroaryl, heteroalkaryl, or any combination thereof;

$R^9$ is optionally interrupted by oxygen, nitrogen, sulfur or any combination thereof;

$R^{10}$ is hydrogen, $C_1$ to $C_4$ alkyl or $C_1$ to $C_4$ alkenyl; and $R^{11}$ is hydrogen, $C_1$ to $C_4$ alkyl or $C_1$ to $C_4$ alkenyl.

Special mention is also made of the following compounds and their salts, including, but not limited to, sodium salts thereof.

Carrier B

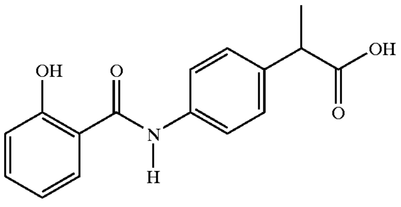

-continued

Carrier C

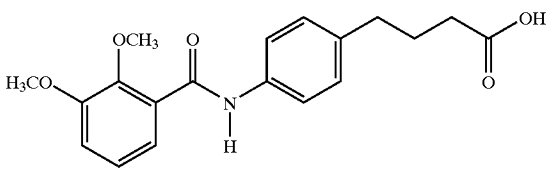

Carrier D

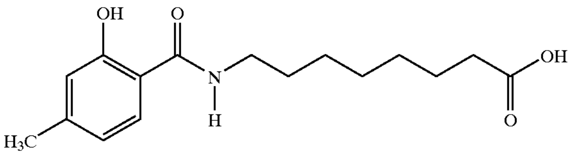

Some preferred delivery agents include, but are not limited to, those described in U.S. Pat. Nos. 4,925,673; 5,451,410; 5,541,155; 5,629,020; 5,643,957; 5,650,386; 5,709,861; 5,714,167; 5,766,633; 5,773,647; 5,792,451; and 5,863,944 and PCT Publication Nos. WO96/12474; WO97/10197; WO97/36480; and WO98/50341.

Acylated amino acids may be prepared by reacting single amino acids, mixtures of two or more amino acids, or amino acid esters with an amine modifying agent which reacts with free amino moieties present in the amino acids to form amides.

Suitable, but not limiting, examples of acylating agents useful in preparing an acylated amino acids include the acid chloride acylating agents having the formula

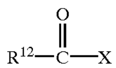

wherein $R^{12}$ is an appropriate group for the modified amino acid being prepared, such as, but not limited to, alkyl, alkenyl, cycloalkyl, or aromatic, and particularly methyl, ethyl, cyclohexyl, cyclophenyl, phenyl, or benzyl; and X is a leaving group. Typical leaving groups include, but are not limited to, halogens such as chlorine, bromine and iodine.

Examples of the acylating agents include, but are not limited to, acyl halides including, but not limited to, acetyl chloride, propyl chloride, cyclohexanoyl chloride, cyclopentanoyl chloride, and cycloheptanoyl chloride, benzoyl chloride, hippuryl chloride and the like; and anhydrides, such as acetic anhydride, propyl anhydride, cyclohexanoic anhydride, benzoic anhydride, hippuric anhydride and the like. Preferred acylating agents include benzoyl chloride. hippuryl chloride, acetyl chloride, cyclohexanoyl chloride, cyclopentanoyl chloride, and cycloheptanoyl chloride.

The amine groups can also be modified by the reaction of a carboxylic acid with coupling agents such as the carbodiimide derivatives of amino acids, particularly hydrophilic amino acids such as phenylalanine, tryptophan, and tyrosine. Further examples include dicyclohexylcarbodiimide and the like.

If the amino acid is multifunctional, i.e., has more than one —OH, —NH, or —SH group, then it may optionally be acylated at one or more functional groups to form, for example, an ester, amide, or thioester linkage.

For example, in the preparation of many acylated amino acids, the amino acids are dissolved in an aqueous alkaline solution of a metal hydroxide, e.g., sodium or potassium hydroxide and the acylating agent added. The reaction time can range from about 1 hour to about 4 hours, preferably about 2 to about 2.5 hours. The temperature of the mixture is maintained at a temperature generally ranging between about 50° C. and about 70° C., preferably between about 10° C. and about 50° C. The amount of alkali employed per equivalent of NH, groups in the amino acids generally ranges between about 1.25 moles and about 3 moles, and is preferably between about 1.5 moles and about 2.25 moles per equivalent of $NH_2$. The pH of the reaction solution generally ranges between about pH 8 and about pH 13, and is preferably between about pH 10 and about pH 12. The amount of amino modifying agent employed in relation to the quantity of amino acids is based on the moles of total free NH, in the amino acids. In general, the amino modifying agent is employed in an amount ranging between about 0.5 and about 2.5 mole equivalents, preferably between about 0.75 and about 1.25 equivalents, per molar equivalent of total NH, groups in the amino acids.

The modified amino acid formation reaction is typically quenched by adjusting the pH of the mixture with a suitable acid, e.g., concentrated hydrochloric acid, until the pH reaches between about 2 and about 3. The mixture separates on standing at room temperature to form a transparent upper layer and a white or off-white precipitate. The upper layer is discarded and modified amino acids are collected by filtration or decantation. The crude modified amino acids are then mixed with water. Insoluble materials are removed by filtration, and the filtrate is dried in vacuo. The yield of modified amino acids generally ranges between about 30 and about 60%, and usually about 45%. The present invention also contemplates amino acids which have been modified by multiple acylation, e.g., diacylation, triacylation, etc.

If amino acid esters or amides are the starting materials, they are dissolved in a suitable organic solvent such as dimethyl formamide or pyridine, and are reacted with the amino modifying agent at a temperature ranging between about 5° C. and about 70° C., preferably about 250° C., for a period ranging between about 7 and about 24 hours. The amount of amino modifying agents used relative to the amino acid esters are the same as described above for amino acids.

Thereafter, the reaction solvent is removed under negative pressure, and optionally, the ester or amide functionality can be removed by hydrolyzing the modified amino acid ester with a suitable alkaline solution, e.g., 1N sodium hydroxide, at a temperature ranging between about 50° C., and about 80° C., preferably about 70° C., for a period of time sufficient to hydrolyze off the ester group and form the modified amino acid having a free carboxyl group. The hydrolysis mixture is then cooled to room temperature and acidified, e.g., with an aqueous 25% hydrochloric acid solution, to a pH ranging between about 2 and about 2.5. The modified amino acid precipitates out of solution and is recovered by conventional means such as filtration or decantation.

The modified amino acids may be purified by acid precipitation, recrystallization, or fractionation on solid column supports. Fractionation my be performed on a suitable solid column supports such as silica gel or alumina, using solvent mixtures such as acetic acid/butanol/water as the mobile phase; reverse phase column supports using trifluoroacetic acid/acetonitrile mixtures as the mobile phase, and ion exchange chromatography using water as the mobile phase. The modified amino acids may also be purified by extraction with a lower alcohol such as methanol, butanol, or isopropanol to remove impurities such as inorganic salts.

The modified amino acids generally are soluble in alkaline aqueous solution (pH≧9.0); partially soluble in ethanol, n-butanol and 1:1 (v/v) toluene/ethanol solution; and insoluble in neutral water. The alkali metal salts, e.g., the sodium salts of the modified amino acids, are generally soluble in water at about a pH of 6–8.

In poly amino acids or peptides, one or more of the amino acids may be modified acylated and/or sulfonated. Poly amino acids and peptides may include one or more acylated amino acid(s). Although linear modified poly amino acids and peptides will generally include only one acylated amino acid, other poly amino acid and peptide configurations can include more than one acylated amino acid. Poly amino acids and peptides can be polymerized with the acylated amino acid(s) or can be acylated after polymerization.

Sulfonated amino acids, poly amino acids, and peptides are modified by sulfonating at least one free amine group with a sulfonating agent which reacts with at least one of the free amine groups present.

Suitable, but non-limiting, examples of sulfonating agents useful in preparing sulfonated amino acids include sulfonating agents having the formula $R^{13}—SO_2—X$ wherein $R^{13}$ is an appropriate group for the modified amino acid being prepared such as, but not limited to, alkyl, alkenyl, cycloalkyl, or aromatics and X is a leaving group as described above. One example of a sulfonating agent is benzene sulfonyl chloride.

Modified poly amino acids and peptides may include one or more sulfonated amino acid(s) and/or acylated amino acids. Although linear modified poly amino acids and peptides used generally include only one sulfonated amino acid, other poly amino acid and peptide configurations can include more than one sulfonated amino acid. Poly amino acids and peptides can be polymerized with the sulfonated amino acid(s) or can be sulfonated after polymerization.

Delivery Systems

The compositions useful herein may include one or more active agents.

In one embodiment, the compounds above or salts of these compounds or poly amino acids or peptides that include at least one of these compounds or salts may be used directly as a delivery carrier by simply mixing one or more compound or salt, poly amino acid or peptide with the active agent prior to administration.

The administration mixtures are prepared by mixing an aqueous solution of the carrier with an aqueous solution of the active ingredient, just prior to administration. Alternatively, the carrier and the biologically or chemically active ingredient can be admixed during the manufacturing process. The solutions may optionally contain additives such as phosphate buffer salts, citric acid, acetic acid, gelatin, and gum acacia.

Stabilizing additives may be incorporated into the carrier solution. With some drugs, the presence of such additives promotes the stability and dispersibility of the agent in solution.

The stabilizing additives may be employed at a concentration ranging between about 0.1 and 5% (w/v), preferably about 0.5% (w/v). Suitable, but non-limiting examples of stabilizing additives include gum acacia, gelatin, methyl cellulose, polyethylene glycol, carboxylic acids and salts thereof, and polylysine. The preferred stabilizing additives are gum acacia, gelatin, and methyl cellulose.

The amount of active agent is an amount effective to accomplish the purpose of the particular active agent for the target indication. The amount of active agent in the compositions typically is a pharmacologically, biologically, therapeutically, or chemically effective amount. However, the amount can be less than a pharmacologically, biologically, therapeutically, or chemically effective amount when the composition is used in a dosage unit form, such as a powder or a liquid, because the dosage unit form may contain a plurality of carrier/biologically or chemically active agent compositions or may contain a divided pharmacologically, biologically, therapeutically, or chemically effective amount. The total effective amount can then be administered in cumulative units containing, in total, pharmacologically, biologically, therapeutically or chemically active amounts of biologically or pharmacologically active agent.

The total amount of active agent, and particularly biologically or chemically active agent, to be used can be determined by those skilled in the art. However, it has surprisingly been found that with some biologically or chemically active agents, the use of the presently disclosed carriers in pulmonary delivery systems provides extremely efficient delivery, Therefore, lower amounts of biologically or chemically active agents than those used in prior dosage unit forms or delivery systems can be administered to the subject, while still achieving the same blood levels and therapeutic effects.

The amount of carrier in the present compositions is a delivery effective amount and can be determined for any particular carrier or biologically or chemically active agent by methods known to those skilled in the art. The effective amounts of the active agent and carrier in the composition may vary over a considerable range and is dependent upon the age, weight, sex, sensitivity, medical history, and the like of the individual. One should take into account the nature of the active agent and carrier, the specific activity of the agent (units of bioactivity/mass), and its rate of absorption in the lung, all of which contribute to a determination of the therapeutically effective dose.

Following administration, the active agent present in the composition or dosage unit form is rapidly taken up into the circulation. The bioavailability of the active agent is readily assessed by measuring a known pharmacological activity in blood, e.g. an increase in blood clotting time caused by heparin, a decrease in circulating calcium levels caused by calcitonin, or blood glucose level variations caused by insulin. Alternatively, the circulating levels of active agent itself can be measured directly.

Alternately, where the target is the lung, delivery is effected automatically. The bioavailability of the active agent is assessed by measuring a known pharmacodynamic parameter of activity.

Dosage unit forms can also include any of excipients, diluents, disintegrants, lubricants, plasticizers, colorants, and dosing vehicles, including, but not limited to water, 1,2-propane diol, ethanol, olive oil, or any combination thereof.

The delivery compositions may also include one or more enzyme inhibitors. Such enzyme inhibitors include, but are not limited to, compounds such as actin in or epiactinonin and derivatives thereof. Derivatives of these compounds are disclosed in U.S. Pat. No. 5,206,384, the disclosure of which is hereby incorporated herein by reference. Other enzyme inhibitors include, but are not limited to, aprotinin (Trasylol) and Bowman-Birk inhibitor.

The system is particularly advantageous for delivering chemically or biologically active agents which would otherwise be destroyed or rendered less effective by conditions encountered before the active agent reaches its target zone (i.e. the area in which the active agent of the delivery composition is to be released) and within the body of the animal to which they are administered. Particularly, the present invention is useful in pulmonary administration, such as by an inhaler, of active agents, especially those which are not ordinarily deliverable by that route or for which improved delivery is desirable. Improved delivery may be observed in a number of ways, including but not limited to, an overall increase in the amount of active agent delivered over time, an overall increase in the biological response over time, and an increased delivery or response at a particular time, such as in quicker delivery of the active agent or quicker response.

DESCRIPTION OF THE PREFERRED EMBODIMENTS

The following examples illustrate the invention without limitation. All parts are given by weight unless otherwise indicated.

EXAMPLE 1

Preparation of Carriers

Preparation of 2-(4-(N-salicyloyl)aminophenyl) propionic acid (Carrier B)

A slurry of 58.6 g (0.355 mol) of 2-(4-aminophenyl) propionic acid and 500 ml of methylene chloride was treated with 90.11 ml (77.13 g. 0–710 mol) of trimethylsilyl chloride and was heated to reflux for 120 min. The reaction mixture was cooled to 0° C. and treated with 184.44 ml (107.77 g, 1.065 mol) of triethylamine. After stirring for 5 minutes, this mixture was treated with a solution of 70.45 g (0.355 mol) of O-acetylsalicyloyl chloride and 150 ml of methylene chloride. The reaction mixture was warmed to 25° C. and stirred for 64 hr. The volatiles were removed in vacuo. The residue was stirred in 2N aqueous sodium hydroxide for one hour and acidified with 2 M aqueous sulfuric acid. The solid was recrystallized twice from ethanol/water to give a tan solid. Isolation by filtration afforded 53.05 g of (52% yield) of 2-(4-(N-salicyloyl) aminophenyl)propionic acid.

Properties. Solubility: 200 mg/ml: 200 mg+350 $\mu$l 2N NaOH+650 $\mu$l $H_2O$—pH –7.67. Anal. calculated for—C, 67.36; H, 5.3; N, 4.91. Found—C, 67.05; H, 5.25; N, 4.72.

Preparation of Sodium 2-(4-(N-salicyloyl) aminophenyl)propionate (Sodium Salt of Carrier B)

A solution of 53.05 g (0.186 mol) of 2-(4-(N-salicyloyl) aminophenyl)propionic acid and 300 ml of ethanol was treated with 7.59 g (0.190 mol) of NaOH dissolved in 22 ml of water. The reaction mixture was stirred for 30 min at 25 C. and for 30 min at 0° C. The resulting pale yellow solid was isolated by filtration to give 52.61 g of sodium 2-(4-(N-salicyloyl)aminophenyl)propionate.

Properties. Solubility: 200 mg/ml clear solution, pH=6.85. Anal. calculated for —C, 60.45; H, 5.45; N, 3.92; Na, 6.43. Found—C, 60.84; H, 5.87; N, 3.85; Na, 6.43. Melting point 236–238° C.

Preparation of the Sodium Salt of Carrier C

A 2 L round bottom flask equipped with a magnetic stirrer and a reflux condenser was charged with a suspension of 3-(4-aminophenyl)propionic acid (15.0 g, 0.084 moles, 1.0 equiv.) in dichloromethane (250 ml). Chlorotrimethylsilane (18.19 g,0.856 moles, 2.0 equiv.) was added in one portion, and the mixture was heated to reflux for 1.5 h under argon. The reaction was allowed to cool to room temperature and was placed in an ice bath (internal temperature<10 C.). The reflux condenser was replaced with an addition funnel containing triethylamine (25.41 g., 0.251 moles, 3.0 equiv.). The triethylamine was added dropwise over 15 min, and a yellow solid formed during the addition. The funnel was replaced by another addition funnel containing a solution of 2,3-dimethoxybenzoylchloride (18.31 g, 0.091 moles, 1.09 equiv.) in dichloromethane (100 mL). The solution was added dropwise over 30 min. The reaction was stirred in the ice bath for another 30 min and at ambient temperature for 3 h. The dicholoromethane was evaporated in vacuo to give a brown oil. The brown oil was cooled in an ice bath, and an ice-cold solution of saturated sodium bicarbonate (250 ml) was added. The ice bath was removed, and the reaction was stirred 1 h to afford a clear brown solution. The solution was acidified with concentrated HCl and stored at ca 5 C. for 1 hour. The mixture was extracted with dichloromethane (3×100 mL), dried over sodium sulfate, the salts filtered off and the dichloromethane removed in vacuo. The resulting solid was recrystallized from 50% ethyl acetate/water (v/v) to afford Carrier C acid as off white needles (25.92 g. 90%). Anal. Calcd. For $C_{19}H_{21}NO_5$: C, 66.46; H, 6.16; N, 4.08; Found: C, 66.14; H, 6.15; N, 3.98. mp=99–102 C.

12 grams of the Carrier C acid was dissolved in ethanol, 75 mL, with warming. To this solution a 8.5 M Sodium hydroxide (1.02 molar equivalents, 1.426 grams in 4.5 mL water) solution was added. The mixture was stirred for 15 minutes. Approximately three quarters of the ethanol was remove in vacuo and n-heptane, 100 mL, was added to the resulting oil causing a precipitate to form. The solids were dried in vacuo at 50° C. Anal. Calc'd. For $C_{19}H_{20}NO_5Na0.067H_2O$: C, 62.25; H, 5.54; N, 3.82; Na, 6.27. Found: C, 62.37; H, 5.77; N, 3.80; Na, 5.75.

Preparation of N-(4-methylsalicyloyl)-8-aminocaprylic acid (Carrier D)

(a) Preparation of Oligo(4-methylsalicylate)

Acetic anhydride (32 mL, 34.5 g, 0.338 mol, 1.03 eq), 4-methylsalicylic acid (50 g, 0.329 mmol, 1.00 eq), and xylenes (100 mL) were added to a 1 L, four-neck flask fitted with a magnetic stir bar, a thermometer, and a condenser. The flask was placed in a sand bath and heating of the cloudy white mixture begun. The reaction mixture cleared to a yellow solution around 90° C. Most of the volatile organics (xylenes and acetic acid) were distilled into the Dean-Stark trap over three hours (135–146° C.). Distillation was continued for another hour (a total of 110 mL distilled), during which the pot temperature slowly rose to 204° C. and the distillate slowed to a trickle. The residue was poured off while still hot into an aluminum tray. Upon cooling a brittle yellow glass formed. The solid was ground to a fine powder. The oligo(4-methylsalicylate) received was used without further purification.

(b) Preparation of N-(4-methylsalicyloyl)-8-aminocaprylic acid

A 7M solution of potassium carbonate (45 mL, 43.2 g, 0.313 mol, 0.95 eq), 8-aminocaprylic acid (41.8 g, 262 mol, 798 eq), and water (20 mL) were added to a 1 L round bottom flask equipped with a magnetic stir bar, condenser, and an addition funnel. The white cloudy mixture was treated with a solution of oligo(4-methylsalicylate) (44.7 g, 0.329 mmol 1.0 eq) and dioxane (250 mL), added over thirty minutes. The reaction mixture was heated to 90° C. for 3 hours (at which time the reaction was determined to have finished, by HPLC). The clear orange reaction mixture was cooled to 30° C. and acidified to pH=2 with 50% aqueous sulfuric acid (64 g). The resulting solid was isolated by filtration. The white solid was recrystallized from 1170 mL of 50% ethanol-water. The solid was recovered by filtration and was dried over 18 hours in a 50° C. vacuum oven. The N-(4-methylsalicyloyl)-8-aminocaprylic acid was isolated as a white solid (30.88 g, 52%); mp=113–114° C.; $^1$H NMR (DMSO-$d_6$) δ12.80 (s, 1H), 12.00 (s, 1H), 8.73 (bt, 1H), 7.72 (d, 1H), 6.70 (s, 1H), 6.69 (d, 1H), 3.26 (q, 2H), 2.26 (s, 3H), 2.19 (t, 2H), 1.49 (m, 4H), 1.29 (m, 6H). Anal. Calcd for $C_{16}H_{23}NO_4$: C, 65.51; H, 7.90; N, 4.77. Found: C, 65.48; H, 7.84; N, 4.69.

EXAMPLE 2

Pulmonary Porcine Insulin Delivery

Materials and Procedures

Materials

Sprague Dawley female rats 225–300 g (Charles River, Raleigh, N.C.)

Fiber optic laryngoscope (Custom Manufactured, EPA, Research Triangle Park, N.C.)

Heating blanket thermostatically control via rectal probe (Harvard Apparatus, Cambridge, HA)

Siliconized Eppendorf tubes

Helix Medical Silicone Tubing

Spray instillator (Penn Century, Philadelphia, Pa.)

Ketamine (100 mg/ml) Lot number 440350 (Fort Dodge Laboratories Inc. Fort Dodge, Iowa)

Xylazine (100 mg/ml) Lot number 116ZZ01 (Vedco Inc. St. Joseph, Mo.)

Acepromazine (10 mg/ml) Lot number 3941077 (Fort Dodge Laboratories Inc. Fort Dodge, Iowa)

Heparin 1000 units/ml Lot number 104067 (Elkins-Sinn, Inc. Cherry Hill, N.J.)

0.9% Sodium Chloride Injection USP sterile solution Lot number PS059113 (Baxter Healthcare Corporation, Deerfield, Ill.)

Lyophilized porcine insulin 25.9 IU/mg (Emisphere Technologies)

Carrier B Na-2-(4-(N-salicyloyl)amino phenyl)propionate (Emisphere Technologies)

Procedures

1. Solutions

A cocktail of anesthetic solution containing Xylazine (100 mg/ml) Ketamine (100 mg/ml): Acepromazine (10 mg/ml) in the proportion of 1:3:1.

0.9% Sodium Chloride Injection USP containing Heparin 20 units/ml

Insulin was dissolved inpH=3 distilled water titrated with 0.01 N HCl. When solution was clear, pH 7 distilled water was added. Then, pH was brought to 7.5 with 0.01 NaOH.

Carrier B was dissolved in distilled water pH 7.4, sonicated for 2 minutes and its pH adjusted to 7.4 using NaOH 0.1N.

2. Animals

Each rat was weighed and identified using an indelible marker and anesthetized by intraperitoneal injection of ketamine: Xylazine: Acepromazine cocktail, at 80 mg/kg, 10 mg/kg and 2.0 mg/kg, respectively and returned to its cage. The rat was transferred to the surgical bench and placed on a heating blanket thermostatically controlled via rectal probe, once deep anesthesia was achieved.

The right jugular vein of each rat was catheterized using silicone tubing and the patency of the catheter was confirmed by slowly flushing the cannula with 200 μl heparin saline and then withdrawing 100 μl of blood. The cannula was then cleared with 200 μl of heparinized saline solution.

An endotracheal tube was inserted using a fiber optic laryngoscope. The syringe (Hamilton syringe) of the instillator was attached to the endotracheal tube and used to instill solution (100 μl) in the airways. The endotracheal tube was removed following administration, and the breathing rate was monitored throughout the remainder of the study.

Blood samples (500 μl) were withdrawn at 0, 10, 30, 60, 90, 120 and 180 min and the cannula flushed with approximately 200 μl of heparinized saline solution. The blood was collected in 1 ml tuberculin syringes (containing 100 μl heparin 20 μ/ml) placed directly into microcentrifuge tubes.

Blood samples were immediately centrifuged at 10000 rpm for 4 min. Aliquots of approximately 30 μl were transferred to labeled siliconized 1 ml Eppendorf tubes and kept on ice until completion of the study for subsequent glucose determination. The remaining samples were frozen at −70° C. for insulin determination (Ultra-sensitive RIA).

Analyses

1. Glucose Determination

Determination of fasting plasma glucose levels was performed using the Ektachem DT Slide (GLU) method. The analysis is based on the enzyme-catalyzed reaction of glucose with molecular oxygen, followed by a second reaction that produces a highly-colored red dye. The intensity of the color is proportional to the amount of glucose in the sample.

2. Pharmacokinetic Analysis

Average insulin plasma concentrations over time were subjected to standard compartmental and non-compartmental pharmacokinetic analysis. Normally, compartmental and non-compartmental analyses are performed simultaneously to demonstrate the validity of the compartmental model.

a. Compartmental analysis

Average insulin concentrations ($C_{INS}$) versus-time profiles upon spray-intratracheal (IT) administration of porcine insulin were fitted to a one-compartment body model, first order absorption using the least-squares nonlinear regression method (PKanalyst, Micromath, Salt Lake City, Utah). Average concentrations of insulin were fitted to the following equation:

$$C_{Pins}=A(e^{-ke\,t}+e^{-ka\,t}) \quad \text{(Eq.1)}$$

where A=D $k_a$/Vd ($k_a$−$k_e$) is the concentration of drug in the body at time zero, $k_a$ is the first order absorption rate constant, $k_e$ is the first order elimination rate constant.

The area under the lung concentration-time curve ($AUC_{0-1}$) was calculated by the trapezoidal rule. Interpolation to infinity was performed by dividing the last $C_{ins}$ measured by the first-order rate constant of the terminal phase. The total area under the curve was estimated by the summation of these two compounds.

The elimination half-life was calculated from 0.693/$k_e$ where $k_e$ is the slope of the terminal phase of the log of the concentration-time profile.

b. Non-compartmental analysis

The non-compartment analysis for insulin plasma concentrations over time was performed using standard techniques. The time to peak $C_{Pins}$ ($T_{max}$) and peak $C_{Pins}$ ($C_{max}$) were determined from the non-fitted average plasma concentrations ($C_{Pins}$) versus-time profiles for the treatments. AUC was calculated by the trapezoidal rule. MRT was not calculated due to a lack of data following intravenous administration from which to calculate pharmacokinetic parameters.

3. Pharmacodynamic Analysis

The percentage minimum plasma glucose concentration (%MPGC) and the time T to attain each %MPGC (T%MPGC) were determined from the average plasma glucose levels versus-time profiles for the treatments.

The area above the curve effect (AACE) was calculated as follows:

$$AAC_E = \text{Total area} - AUC_E \quad \text{(Eq.2)}$$

where $AUC_E$ represents the area under the curve effect calculated using the trapezoidal rule.

The percentage total reduction in plasma glucose from 0→t (%TRPG 0→t) was determined using the following equation:

$$\%TRPG\ 0 \rightarrow t = 100\ (AAC_E/\text{total area}) \quad \text{(Eq.3)}$$

4. Statistical Analysis

Differences in AUCs between insulin doses were tested for significance using Sheffe's multiple comparison test assuming alpha<0.05. Differences in $AACE_{3\rightarrow 3}$ (glucose plasma levels) between insulin alone and combined with Carrier B was tested for significance using Turkey's test and analysis of variance assuming alpha<0.05.

Figure 1:
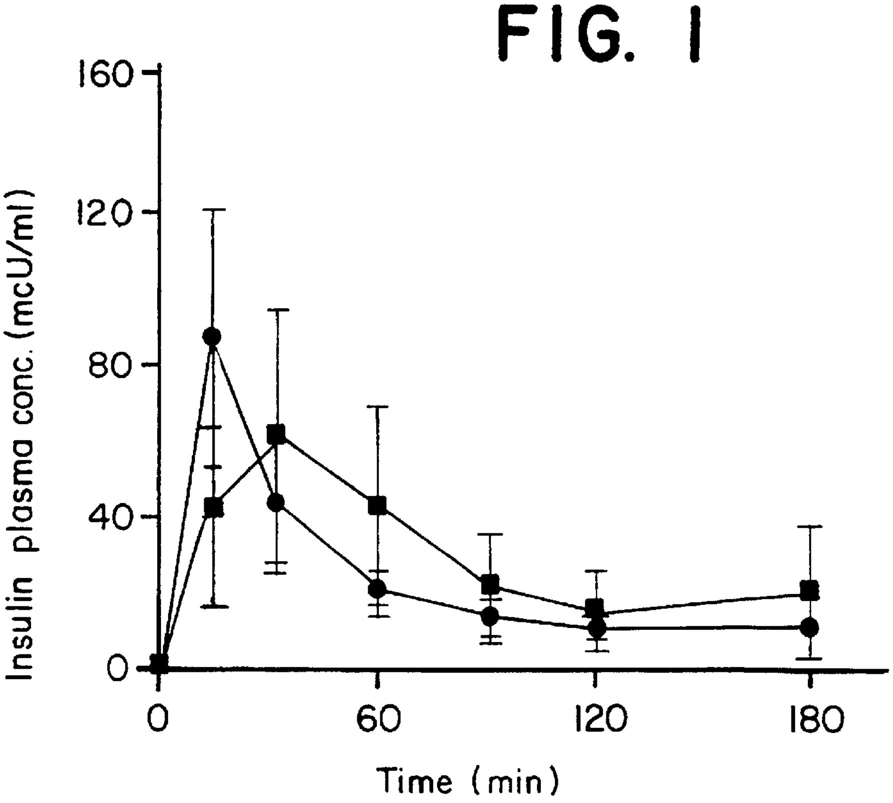
FIG. 1 is a graphical illustration of plasma insulin-time profiles following lung spray-IT instillation of insulin alone 0.05 mg/kg (0.13 U/kg) (♦) and combined with Carrier B 5 mg/kg (■). Bars represent ±SD n=5.
Figure 2:
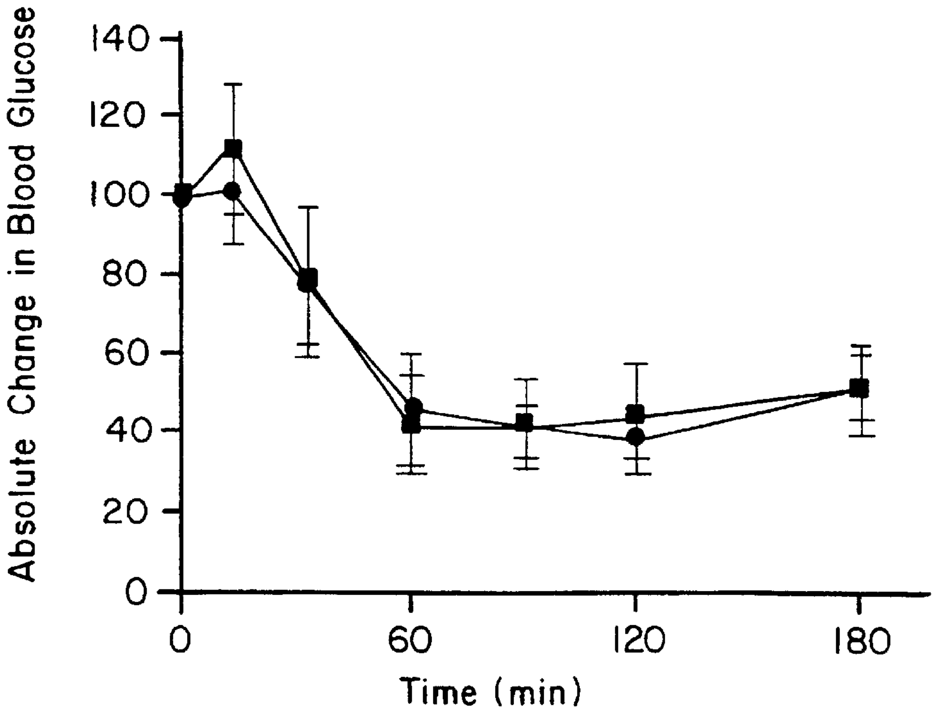
FIG. 2 is a graphical illustration of plasma glucose-time profiles following lung spray-IT instillation of insulin alone 0.05 mg/kg (0.13 U/kg) (♦) and combined with Carrier B 5 mg/kg (■). Bars represent ±SD n=5.

EXAMPLE 2a (i) The plasma insulin and plasma glucose-time profiles following lung spray-intratracheal [IT] instillation of insulin 0.05 mg/kg combined with Carrier B 5 mg/kg are shown in FIGS. 1 and 2, respectively.

Figure 3:
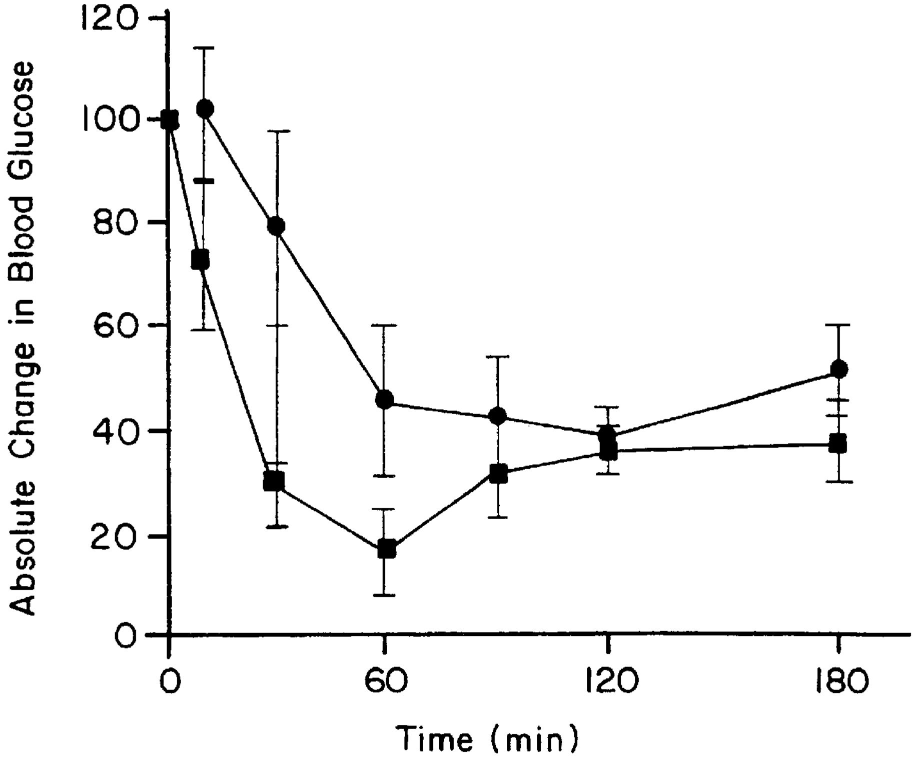
FIG. 3 is a graphical illustration of plasma glucose-time profiles following lung spray-IT instillation of insulin alone.

(ii) and (iii) FIGS. 3 and 4 and Table 1, below show the plasma glucose-time profiles and Pharmacodynamic parameters following lung spray-IT instillation of Carrier B 16 mg/kg combined with insulin 0.05 and 0.01 mg/kg respectively. A significant difference (p<0.05) in the $AACEO_{0\rightarrow 3}$ in the presence and absence of carrier for both doses of insulin was observed. The $\%TRGP_{0\rightarrow 3}$ increased from 10.5±1.5 to 36±9% and from 47±10 to 65.7±5% for the 0.01 and 0.05 doses of insulin (combined with 16 mg/kg of Carrier B), respectively. No significant difference in $\%TRGP_{0\rightarrow 3}$ was observed between insulin alone at 0.05 mg/kg and combined with carrier B 5 mg/kg. This dose-effect relationship found for Carrier B is most likely due to its effect on the pharmacokinetics of insulin (increased bioavailability).

TABLE 1

| | Porcine Insulin dose (mg/kg) and Carrier B (mg/kg) | | | | |
|---|---|---|---|---|---|
| | Insulin alone 0.01 | Insulin 0.01 & Carrier B 16 mg/kg | Insulin alone 0.05 | Insulin 0.05 & Carrier B (5 mg/kg) | Insulin 0.05 & Carrier B (16 mg/kg) |
| % MPGC | 70.02 | 46.4 | 35.7 | 38.6 | 14.9 |
| T % MPGC (min) | 180 | 90 | 120 | 90 | 60 |
| % $TRPG_{0-3\ hr}$ | 10.5 ± 1.5 | 36 ± 9 | 47 ± 10 | 46 ± 8 | 65.7 ± 5 |
| $AACE_{0-t}$ (mcU/min/ml) | 1892 ± 989 | 6395 ± 1609 | 8497 ± 1716 | 8218 ± 1430 | 11834 ± 872 |

These data suggest the potential of Carrier B to increase significantly the bioavailability of insulin and its effect on the glucose levels.

(iv) Average insulin plasma concentrations following spray-IT instillation as a function of insulin dose is shown in FIG. 5. The pharmacokinetic parameters resulting from the compartmental and non-compartmental analysis are listed in Table 2, below. Non-linear curve fitting of the average plasma levels indicated that the fall in plasma concentrations was best described by a monoexponential decline with first order absorption in all cases. The evaluation of goodness of fit was done by comparing the respective model selection criteria (MSC). This modified Akaike information criterion allows the comparison of the appropriateness of a model. MSC values range from 1.3 to 3.8 indicating the appropriateness of the model.

Average peak plasma concentration achieved in these studies were 57.5 $\mu$U/ml ($T_{max}$=10 min), 18.8 $\mu$U/ml ($T_{max}$=20 min), 71.3 $\mu$U/ml ($T_{max}$=10 min), 48.95 $\mu$U/ml ($T_{max}$=10.0 min), 213.1 $\mu$U/ml ($T_{max}$=10), 354 $\mu$U/ml ($T_{max}$=20), and 902 $\mu$U/ml ($T_{max}$=20) for the 0.001 mg/kg (0.026 U/kg), 0.005 (0.13 U/kg), 0.01 (0.26 U/kg), 0.05 (1.3 U/kg), 0.1 (2.6 (U/kg), 0.5 and 1 mg/kg of porcine insulin, respectively and are in close agreement with those obtained after curve fitting.

The log plasma concentration-time plots as a function of insulin dose (FIG. 5) showed a decline in plasma concentrations with a defined half-life significantly longer (from 27.8 to 142.4, min see Table 2) than that previously reported following intravenous administration of 0.1 u/kg bovine insulin to rabbits (t ½=30 min). This observation suggests the presence of a "flip-flop" case, which occurs when absorption rather than elimination dictates the decline in plasma concentrations. This increase in absorption half-life does not imply however, that absorption is the rate-limiting step. Rather, this event may be the result of the slow "dissolution" or transformation of insulin from the hexameric to the monomeric form as the concentration of insulin in the instilled volume increases.

The area under the curve to infinity ($AUC_{0\rightarrow\infty}$) calculated using the trapezoidal rule was 2930, 1334, 5050, 5260, 15374, 67676, and 200230 $\mu$U min/ml for the 0.001 mg/kg (0.026 U/kg), 0.005 (0.13 U/kg), 0.01 (0.26 U/kg), 0.05 (1.3 U/kg), 0.1 (2.6 (U/kg), 0.5 and 1 mg/kg of porcine insulin, respectively.

Multiple comparison among doses using Sheffe's test revealed no significant difference (p>0.05) in the AUC values. This lack of significance is likely to be due to the high intra subject variability (see, SD for AUC in Table 2). The relative bioavailability of the insulin used can be calculated assuming that the extent of absorption of porcine insulin following pulmonary administration and human insulin following subcutaneous (SC) are equivalent. Based on this assumption, the relative bioavailability of porcine insulin is 12.46%.

TABLE 2

| | Porcine Insulin dose (mg/kg) | | | | | | |
|---|---|---|---|---|---|---|---|
| | 0.001 | 0.005 | 0.01 | 0.05 | 0.1 | 0.5 | 1.0 |
| Compartmental analysis | | | | | | | |
| Cmax ($\mu$U/ml) | 57.2 | 16.46 | 70.5 | 48.3 | 188.08 | 381.8 | 891.3 |
| Tmax (min) | 10.8 | 12.4 | 11.9 | 14 | 13.7 | 31.3 | 13.32 |
| $AUC_{0\rightarrow\infty}$ ($\mu$U.min/ml) | 2930 | 1334 | 5049 | 5260 | 15374 | 67676 | 2000230 |
| $k_e$ ($min^{-1}$) | 0.23 | 0.23 | 0.25 | 0.23 | 0.23 | 0.1 | 0.3 |
| $t_{1/2}$ (elim)(min) | 3.0 | 3.0 | 3.0 | 3.0 | 3.0 | 7.8 | 2.1 |
| $k_a$ ($min^{-1}$) | 0.025 | 0.016 | 0.018 | 0.0105 | 0.012 | 0.007 | 0.005 |
| $t_{1/2}$ (abs)(min) | 27.8 | 42.6 | 38.0 | 65.9 | 59.9 | 100.8 | 142.4 |

TABLE 2-continued

| | Porcine Insulin dose (mg/kg) | | | | | | |
|---|---|---|---|---|---|---|---|
| | 0.001 | 0.005 | 0.01 | 0.05 | 0.1 | 0.5 | 1.0 |
| Non-compartmental analysis | | | | | | | |
| $C_{max}$ (ng/ml) | 57.5 | 18.8 | 71.3 | 48.95 | 213.1 | 354.1 | 902.8 |
| $t_{max}$ (h) | 10 | 20 | 10 | 10 | 10 | 60 | 20 |
| $AUC_{0\rightarrow\infty}$ ($\mu$U.min/ml) | 1695 | 1176 | 4995 | 5288 | 17907 | 65077 | 199818 |

The plasma glucose-time profiles and PD data for the various doses of insulin instilled are shown in FIG. 6 and Table 3, below. The results show that an increase in dose (from 0.01 to 1 mg/kg) produced a significant decrease in the percentage minimum plasma glucose (%MPGC) from 70.2 to 13.1, without changing significantly the time T to reach this minimum (T%MPGC). The total reduction in plasma glucose from 0 to 3 hr (%$TRPG_{0\rightarrow3\ hr}$) (See Table 3) increase significantly from 10.5 to 73.7% indicating that a greater bioavailability was achieved with an increase in the extent of absorption as the insulin dose was increased.

TABLE 3

| | Porcine Insulin dose (mg/kg) | | | | |
|---|---|---|---|---|---|
| | 0.01 | 0.05 | 0.1 | 0.5 | 1.0 |
| % MPGC | 70.2 | 35.69 | 35.3 | 30.6 | 13.1 |
| T % MPGC | 180 | 120 | 120 | 60 | 120 |
| % $TRPG_{0-3\ hr}$ | 10.5 ± 1.5 | 47.2 ± 9.5 | 50.5 ± 12.7 | 54.5 ± 6.5 | 73.7 ± 3.1 |
| $AACE_{0-t}$ ($\mu$U.min/ml) | 1892 ± 989 | 8497 ± 1716 | 9102 ± 2295 | 10205 ± 1173 | 13266 ± 570 |

The intersubject variability in the glucose response (CV<30%) was smaller than the insulin response. Thus, there is a dampening of the insulin variability as the hormone's appearance in the circulation is translated into its biological activity.

EXAMPLE 2b

A composition of 0.05 mg/kg of porcine insulin and 16 mg/kg of Carrier B was administered to rats by lung spray-IT instillation. A composition of 0.05 mg/kg porcine insulin alone was also administered to rats by lung spray-IT instillation. Results are illustrated in FIG. 7 and in Tables 4 and 5.

TABLE 4

| | With Carrier B | | Without Carrier B | |
|---|---|---|---|---|
| Time (min) | Average Insulin Concentration (mcU/mL ± stdev) | AUC | Average Insulin Concentration (mcU/mL ± stdev) | AUC |
| 0 | 0 | 10347.35 | 0 | 4300.025 |
| 10 | 157.67 ± 32.86 | | 87.28 ± 34.34 | |
| 30 | 101.36 ± 35.14 | | 43.64 ± 17.96 | |
| 60 | 70.48 ± 30.31 | | 21.50 ± 3.80 | |
| 90 | 44.17 ± 8.97 | | 14.13 ± 4.49 | |

TABLE 4-continued

| | With Carrier B | | Without Carrier B | |
|---|---|---|---|---|
| Time (min) | Average Insulin Concentration (mcU/mL ± stdev) | AUC | Average Insulin Concentration (mcU/mL ± stdev) | AUC |
| 120 | 37.28 ± 15.47 | | 10.89 ± 3.31 | |
| 180 | 11.04 ± 3.21 | | 11.38 ± 9.54 | |

TABLE 5

PK parameters following lung spray-IT instillation of insulin combined with carrier B and to the lungs of rats

| | Porcine Insulin dose (mg/kg) | | |
|---|---|---|---|
| | 0.01 | 0.05 | 0.05 |
| | Carrier B dose (mg/kg) | | |
| | 16 | 5 | 16 |
| Compartmental Analysis (average data) | | | |
| Cmax ($\mu$U/ml) | 31 | 54 | 147 |
| Tmax (min) | 11 | 15 | 13 |
| $AUC_{0\rightarrow\infty}$ ($\mu$U min/ml) | 1805 | 6189 | 10666 |
| $k_e$ ($min^{-1}$) | 0.21 | 0.21 | 0.21 |
| $t_{1/2}$ (elim) (min) | 2.8 | 3.3 | 3.3 |
| $k_a$ ($min^{-1}$) | 0.022 | 0.010 | 0.017 |
| $t_{1/2}$ (abs) (min) | 31 | 69 | 40 |
| Non-compartmental analysis | | | |
| $C_{max}$ ($\mu$U/ml) | 31.41 | 60.7 | 158 |
| $t_{max}$ (min) | 10 | 30 | 10 |
| $AUC_{0\rightarrow\infty}$ ($\mu$U min/ml) | 1705 ± 126 | 5256 ± 3271 | 10347 ± 3089 |

Comparative Example 2c

Compositions of porcine insulin in escalating doses as shown in Table 6, below were administered to rats by lung spray-IT instillation. Results are illustrated in FIG. 8 and Tables 6 and 7.

TABLE 6

PK parameters following spray-IT instillation of escalating doses of porcine insulin to the lungs of rats

| | Porcine Insulin dose (mg/kg) | | | | |
|---|---|---|---|---|---|
| | 0.01 | 0.05 | 0.1 | 0.5 | 1.0 |
| **Compartmental Analysis (average data)** | | | | | |
| Cmax (μU/ml) | 6.5 | 74 | 141 | 566 | 1634 |
| Tmax (min) | 11.3 | 11.6 | 12.4 | 16.3 | 25 |
| $AUC_{0\to\infty}$ (μU min/ml) | 440 | 3989 | 9111 | 83404 | 223595 |
| $k_e$ ($min^{-1}$) | 0.25 | 0.21 | 0.20 | 0.21 | 0.21 |
| t½ (elim) (min) | 2.8 | 3.3 | 3.3 | 3.3 | 3.3 |
| $k_a$ ($min^{-1}$) | 0.018 | 0.024 | 0.02 | 0.008 | 0.009 |
| t½ (abs) (min) | 39 | 28 | 35 | 90 | 76 |
| **Non-compartmental analysis** | | | | | |
| $C_{max}$ (μU/ml) | 6 | 87 | 152 | 581 | 1926 |
| $t_{max}$ (min) | 10 | 10 | 10 | 30 | 30 |
| $AUC_{0\to\infty}$ (μU min/ml) | 503 ± 93 | 4300 ± 1114 | 9517 ± 3255 | 60344 ± 16406 | 178177 ± 17152 |

TABLE 7

Insulin Plasma Concentrations (mcU/ml)

| Time | Insulin Dose (mg/kg) | | | | | Standard Deviation | | | | |
|---|---|---|---|---|---|---|---|---|---|---|
| (min) | 0.01 | 0.05 | 0.1 | 0.5 | 1 | 0.01 | 0.05 | 0.1 | 0.5 | 1 |
| 0 | 0 | 0 | 0 | 0 | 0 | 0 | 0 | 0 | 0 | 0 |
| 10 | 5.1 | 87.3 | 152 | 443.7 | 1198 | 2.76 | 34 | 36.8 | 214 | 220.6 |
| 30 | 4.12 | 43.6 | 91.2 | 580.5 | 1925 | 1.28 | 18 | 20.5 | 220 | 465.6 |
| 60 | 3.87 | 21.5 | 50.6 | 553.3 | 1056 | 2.76 | 3.9 | 21.6 | 219 | 304 |
| 90 | 2.27 | 14.13 | 48.7 | 275.1 | 681.7 | 0.87 | 4.5 | 38.4 | 136 | 46.9 |
| 120 | 1.87 | 10.9 | 31.1 | 211 | 919.3 | 1.57 | 3.3 | 20.9 | 88 | 323.6 |
| 180 | 1.43 | 11.4 | 19.3 | 161 | 618.3 | 0.37 | 9.5 | 5.38 | 97.6 | 216.3 |
| AUC | 490.75 | 4300.9 | 9517.5 | 60345 | 178143.5 | | | | | |

EXAMPLE 2d

A composition of 0.05 mg/kg of porcine insulin at 5 mg/kg of Carrier B was administered to rats by lung spray-IT instillation. A composition of 0.05 mg/kg porcine insulin alone was also administered by lung spray-IT instillation. Insulin plasma levels are illustrated in FIG. 9 and Tables 5 and 8.

TABLE 8

| | With Carrier B | | Without Carrier B | |
|---|---|---|---|---|
| Time (min) | Average Insulin Concentration (mcU/mL ± stdev) | AUC | Average Insulin Concentration (mcU/mL ± stdev) | AUC |
| 0 | 0 | 5256.463 | 0 | 4300.025 |
| 10 | 40.49 ± 23.30263 | | 87.28 ± 34.34 | |
| 30 | 60.70 ± 33 | | 43.64 ± 17.96 | |
| 60 | 41.22 ± 27.10568 | | 21.50 ± 3.80 | |
| 90 | 21.08 ± 14.46818 | | 14.13 ± 4.49 | |
| 120 | 15.25 ± 15.31622 | | 10.89 ± 3.31 | |
| 180 | 19.22 ± 16.82827 | | 11.38 ± 9.54 | |

EXAMPLE 2e

A composition of 0.01 mg/kg of porcine insulin and 16 mg/kg of Carrier B was administered to rats by lung spray-IT instillation. A composition of 0.01 mg/kg porcine insulin also administered to rats by lung spray-IT instillation. Insulin plasma levels are illustrated in FIG. 10 and in Tables 5 and 9.

TABLE 9

| | With Carrier B | | Without Carrier B | |
|---|---|---|---|---|
| Time (min) | Average Insulin Concentration (mcU/mL ± stdev) | AUC | Average Insulin Concentration (mcU/mL ± stdev) | AUC |
| 0 | 0 | 1705.418 | 0 | 502.5 |
| 10 | 31.41 ± 8.31 | | 5.89 ± 2.76 | |
| 30 | 16.41 ± 4.29 | | 4.12 ± 1.28 | |
| 60 | 10.98 ± 6.09 | | 3.87 ± 2.76 | |
| 90 | 4.87 ± 1.19 | | 2.27 ± 0.87 | |
| 120 | 5.03 ± 1.74 | | 1.87 ± 1.57 | |
| 180 | 4.07 ± 2.73 | | 1.43 ± 0.37 | |

EXAMPLE 3

Pulmonary Porcine Insulin Delivery

EXAMPLE 3a

A pulmonary delivery dosing composition of 0.1 mg/kg of porcine insulin and 7.5 mg/kg of Carrier B sodium salt in water was prepared. Control dosing compositions of 0.1 mg/kg insulin alone and of 7.5 mg/kg Carrier B sodium salt alone were also prepared. A 0.3 ml/kg dose of the pulmonary dosing composition at pH 7.3–7.6 was administered to five normal, non-fasting rats by the following procedure. 1½ Popper and Sons gavage needles were inserted about a few centimeters down the animals' throats. The tip of the needle was manipulated towards the animals' ventral sides where the needle could fall into a pocket and then with further manipulation the trachea. Once the needle was in the trachea, the dosing solution was delivered through the needle.

Periodic blood samples were drawn via the tail artery, and blood glucose levels were measured using Ektachem DT slides (Johnson & Johnson Clinical Diagnostics, Inc., Rochester N.Y.).

Results are illustrated in FIG. 11 for 0.1 mg insulin with 7.5 mg/kg Carrier B sodium salt (■), 0.1 mg/kg insulin alone (●), and 7.5 mg/kg Carrier B sodium salt alone (▲).

EXAMPLE 3b

The procedure of Example 3a was repeated substituting dosing compositions of 0.5 mg/kg of porcine insulin and 7.5 mg/kg of Carrier B sodium salt, in water for the dosing composition at pH 6.6–6.9. Dosing compositions of 0.5 mg/kg insulin alone and of 7.5 mg/kg Carrier B sodium salt alone were also prepared.

Results are illustrated in FIG. 12, where (■) represents 0.5 mg/kg insulin with 7.5 mg/kg Carrier B sodium salt; (●) represents 0.5 mg/kg insulin alone; and (▲) represents 7.5 mg/kg Carrier B sodium salt alone.

EXAMPLE 4

Pulmonary Insulin Delivery

Carrier compound B, carrier compound C sodium salt, and carrier compound D in Table 10 were tested as follows. Each rat was weighed and identified using an indelible marker and anesthetized by intramuscular injection of thorazine (3 mg/kg) and ketamine (44 mg/kg).

An endotracheal tube (spray instillator from Penn Century of Philadelphia, Pa.) with a syringe (Hamilton syringe) attached to the endotracheal tube was inserted using a fiber optic laryngoscope. The syringe (Hamilton syringe) of the instillator was used to instill 0.4 ml/kg of a solution containing insulin (0.03 mg/kg) and a carrier compound (16 mg/kg) into the lower portions of the airway. The endotracheal tube was removed following administration, and the breathing rate was monitored throughout the remainder of the study.

Blood samples were withdrawn at 0, 5, 15, 30, 60, and 120 minutes via the tail artery and assayed with a DSL Insulin Kit #10-1600 following the procedure outlined in the kit. The serum insulin levels are illustrated in FIG. 13 and the $C_{max}$ are illustrated in Table 10 below.

TABLE 10

| Carrier | Cmax (μU/ml) |
|---|---|
| B | 44.6 ± 10.0 |
| C sodium salt | 22.5 ± 4.0 |
| D | 58.8 ± 12.0 |
| None | 19.4 ± 4.3 |

The above mentioned patents, applications, test methods, and publications are hereby incorporated by reference in their entirety.

Many variations of the present invention will suggest themselves to those skilled in the art in light of the above detailed description. All such obvious variations are within the full intended scope of the appended claim.

What is claimed is:

1. A method for administering a biologically-active agent to an animal in need of said agent, said method comprising administering via the pulmonary route to said animal a composition comprising (A) an active agent and (B) a carrier comprising an acylated amino acid, a sulfonated amino acid, a polyamino acid which includes an acylated amino acid, a polyamino acid which include a sulfonated amino acid, or any combination of any of the foregoing.

2. A method as defined in claim 1 wherein said active agent is selected from the group consisting of a biologically active agent, a chemically active agent, or a combination thereof.

3. A method as defined in claim 2, wherein said biologically active agent comprises at least one peptide, mucopolysaccharides, carbohydrate, or lipid.

4. A method as defined in claim 3, wherein said biologically active agent is selected from the group consisting of growth hormones, human growth hormones (hGH), recombinant human growth hormones (rhGH), bovine growth hormone, porcine growth hormones, growth hormone-releasing hormones, interferons, α-interferon, β-interferon, γ-interferon, interleukin-1, interleukin-II, insulin, insulin-like growth factor (IGF), IGF-1, heparin, unfractionated heparin, heparinoids, dermatans, chondroitins, low molecular weight heparin, very low molecular weight heparin, ultra low molecular weight heparin, calcitonin, salmon calcitonin, eel calcitonin, human calcitonin, erythropoietin (EPO), atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoietin, filgrastim, prostaglandins, cyclosporin, vasopressin, sodium chromoglycate, disodium chromoglycate, vancomycin, desferrioxamine (DFO), parathyroid hormone (PTH), fragments of PTH, antimicrobials, anti-fungal agents, analogs, fragments, mimetics and polyethylene glycol (PEG)-modified derivatives of these compounds; and any combination thereof.

5. A method as defined in claim 3, wherein said biologically active agent is selected from the group consisting of human growth hormones (hGH), recombinant human growth hormones (rhGH), bovine growth hormone, growth hormone-releasing hormones, interferons, α-interferon, β-interferon, γ-interferon, interleukin-1, interleukin-II, insulin, insulin-like growth factor (IGF), IGF-1, heparin, unfractionated heparin, heparinoids, low molecular weight heparin, very low molecular weight heparin, ultra low molecular weight heparin, calcitonin, salmon calcitonin, eel calcitonin, human calcitonin, erythropoietin (EPO), atrial naturetic factor, antigens, monoclonal antibodies, somatostatin, adrenocorticotropin, gonadotropin releasing hormone, oxytocin, leutinizing-hormone-releasing-hormone, follicle stimulating hormone, glucocerebrosidase, thrombopoietin, filgrastim, prostaglandins, cyclosporin, vasopressin, sodium chromoglycate, disodium chromoglycate, vancomycin, desferrioxamine (DFO), parathyroid hormone (PTH), fragments of PTH, antimicrobials, anti-fungal agents, analogs, fragments, mimetics and polyethylene glycol (PEG)-modified derivatives of these compounds; and any combination thereof.

6. A method as defined in claim 3, wherein said biologically active agent comprises an interferon, interleukin-II, insulin, insulin-like growth factor (IGF), JGF-1, heparin, low molecular weight heparin, low molecular weight heparin, calcitonin, oxytocin, vasopressin, vancomycin, desferrioxamine, parathyroid hormone, and combinations thereof.

7. A method as defined in claim 2, wherein said biologically active agent selected from the group consisting of insulin, insulin-like growth factor (IGF), IGF-1, or combinations thereof.

8. The method of claim 1, wherein the carrier comprises a compound having the formula

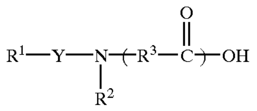

wherein $R^1$ is $C_1$–$C_7$ alkyl, $C_3$–$C_{10}$ cycloalkyl, cycloalkenyl, aryl, thienyl, phenyl, naphthyl, pyrrolo, or pyridyl;

$R^1$ is optionally substituted with one or more $C_1$–$C_7$ alkyl, $C_2$–$C_7$ alkenyl, $C_2$–$C_7$ alkynl, $C_6$–$C_{10}$ cycloalkyl, phenyl, phenoxy, F, Cl, Br, —OH, —$SO_2$, —$SO_3H$, —$NO_2$, —SH, —$PO_3H$, oxazolo, isoxazolo, alkoxy having the formula —$OR^6$, —$COOR^7$, —$N(R^5)_2$, —$N^+(R^5)_3X^-$, or any combination thereof;

Y is

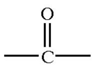

or —$SO_2$—;

X is halogen, hydroxide, sulfate, tetrafluoroborate, or phosphate;

$R^2$ is hydrogen, $C_1$–$C_4$ alkyl, $C_2$–$C_4$ alkenyl, or —$(CH_2)_n$—COOH, where n is 1 to 10;

$R^3$ is $C_1C_{24}$ alkyl, $C_2$–$C_{24}$ alkenyl, $C_2$–$C_{24}$ alkyne, $C_3$–$C_{10}$ cycloalkyl, $C_3$–$C_{10}$ cycloalkenyl, phenyl, naphthyl, ($C_1$–$C_{10}$ alkyl) phenyl, ($C_2$–$C_{10}$ alkenyl) phenyl, ($C_1$–$C_{10}$ alkyl) naphthyl, ($C_2$–$C_{10}$ alkenyl) naphthyl, phenyl ($C_1$–$C_{10}$ alkyl), phenyl ($C_2$–$C_{10}$ alkenyl), naphthyl ($C_1$–$C_{10}$ alkyl) or naphthyl ($C_2$–$C_{10}$ alkenyl);

$R^3$ being optionally substituted with $C_1$–$C_4$ alkyl, $C_2$–$C_4$ alkenyl, $C_1$–$C_4$ alkoxy, —OH, —SH, halogen, —$NH_2$, —$CO_2R^4$, $C_3$–$C_{10}$ cycloalkyl, $C_3$–$C_{10}$ cycloalkenyl, heterocyclic having 3–10 ring atoms wherein the hetero atom is one or more of N, O, S or any combination thereof, aryl, ($C_1$–$C_{10}$ alk)aryl, ar($C_1$–$C_{10}$ alkyl), or any combination thereof;

$R^4$ is hydrogen, $C_1$–$C_4$ alkyl, or $C_2$–$C_4$ alkenyl;

$R^5$ is hydrogen or $C_1$–$C_{10}$ alkyl;

$R^6$ is $C_1$–$C_{10}$ alkyl, alkenyl, alkynyl, aryl or cycloalkyl; and $R^7$ is hydrogen, $C_1$–$C_{10}$ alkyl, alkenyl, alkynl, aryl or cycloalkyl.

9. The method of claim 8, wherein the active agent is selected from the group consisting of insulin, insulin-like growth factor (IGF), IGF-1, or combinations thereof.

10. The method of claim 1, wherein the carrier comprises a compound having the formula Ar—Y—$(R^8)_n$—OH, wherein Ar is a substituted or unsubstituted phenyl or naphthyl, preferably Ar is substituted or unsubstituted 2-OH-phenyl;

Y is

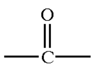

or —$SO_2$—;

$R^8$ has the formula

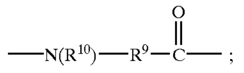

$R^9$ is $C_1$ to $C_{24}$ alkyl, $C_1$ to $C_{24}$ alkenyl, phenyl, naphthyl, ($C_1$ to $C_{10}$ alkyl) phenyl, ($C_1$–$C_{10}$ alkenyl) phenyl, ($C_1$ to $C_{10}$ alkyl) naphthyl, ($C_1$ to $C_{10}$ alkenyl) naphthyl, phenyl ($C_1$ to $C_{10}$ alkyl), phenyl ($C_1$ to $C_{10}$ alkenyl), naphthyl ($C_1$ to $C_{10}$ alkyl) and naphthyl ($C_1$ to $C_{10}$ alkenyl);

$R^9$ is optionally substituted with $C_1$ to $C_4$, alkyl, $C_1$ to $C_4$ alkenyl, $C_1$ to $C_4$ alkoxy, —OH, —SH, —$CO_2R^{11}$, cycloalkyl, cycloalkenyl, heterocyclic alkyl, alkaryl, heteroaryl, heteroalkaryl, or any combination thereof;

$R^9$ is optionally interrupted by oxygen, nitrogen, sulfur or any combination thereof;

$R^{10}$ is hydrogen, $C_1$ to $C_4$ alkyl or $C_1$ to $C_4$ alkenyl; and $R^{11}$ is hydrogen, $C_1$ to $C_4$ alkyl or $C_1$ to $C_4$ alkenyl.

11. The method of claim 10, wherein the active agent is selected from the group consisting of insulin, insulin-like growth factor (IGF), IGF-1, or combinations thereof.

12. The method of claim 1, wherein the carrier comprises a compound having the formula

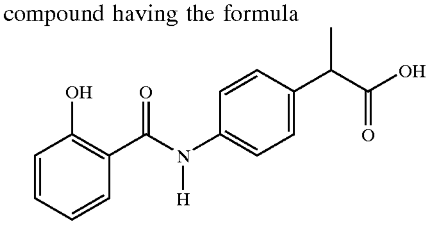

and salts thereof.

13. The method of claim 12, wherein the active agent is selected from the group consisting of insulin, insulin-like growth factor (IGF), IGF-1, or combinations thereof.

14. The method of claim 1, wherein the carrier comprises a compound having the formula

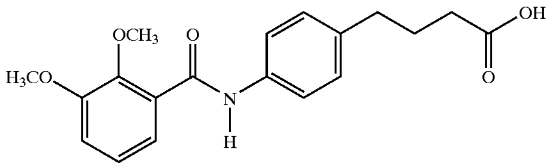

or a salt thereof.

15. The method of claim 14, wherein the active agent is selected from the group consisting of insulin, insulin-like growth factor (IGF), IGF-1, or combinations thereof.

16. The method of claim 1, wherein the carrier comprises a compound having the formula

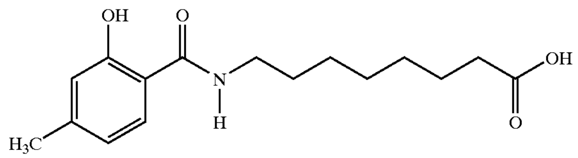

or a salt thereof.

17. The method of claim 16, wherein the active agent is selected from the group consisting of insulin, insulin-like growth factor (IGF), IGF-1, or combinations thereof.

* * * * *